US010183058B2

(12) United States Patent
Averback

(10) Patent No.: US 10,183,058 B2
(45) Date of Patent: Jan. 22, 2019

(54) METHOD OF PREVENTING OR REDUCING THE PROGRESSION OF PROSTATE CANCER

(71) Applicant: Nymox Corporation, Nassau, New Providence (BS)

(72) Inventor: Paul Averback, Nassau (BS)

(73) Assignee: NYMOX CORPORATION, Nassau (BS)

( * ) Notice: Subject to any disclaimer, the term of this patent is extended or adjusted under 35 U.S.C. 154(b) by 59 days.

(21) Appl. No.: 15/185,344

(22) Filed: Jun. 17, 2016

(65) Prior Publication Data

US 2017/0360885 A1 Dec. 21, 2017

(51) Int. Cl.
*A61K 38/10* (2006.01)
*A61K 38/17* (2006.01)
*A61P 35/00* (2006.01)

(52) U.S. Cl.
CPC .......... *A61K 38/1709* (2013.01); *A61K 38/10* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 5,830,670 A | 11/1998 | de la Monte et al. | |
| 5,948,634 A | 9/1999 | de la Monte et al. | |
| 5,948,888 A | 9/1999 | de la Monte et al. | |
| 6,071,705 A | 6/2000 | Wands et al. | |
| 6,660,830 B1 | 12/2003 | Radulescu | |
| 6,924,266 B2 | 8/2005 | Averback | |
| 7,192,929 B2 | 3/2007 | Averback | |
| 7,241,738 B2 | 7/2007 | Averback et al. | |
| 7,317,077 B2 | 1/2008 | Averback et al. | |
| 7,408,021 B2 | 8/2008 | Averback et al. | |
| 7,642,063 B2 | 1/2010 | Samoylova | |
| 8,303,957 B2 | 11/2012 | Firat | |
| 9,243,035 B2 | 1/2016 | Averback et al. | |
| 2003/0054990 A1 | 3/2003 | Averback | |
| 2003/0109437 A1* | 6/2003 | Averback ........... | C07K 14/4711 424/134.1 |
| 2007/0237780 A1 | 10/2007 | Averback et al. | |
| 2009/0286742 A1 | 11/2009 | Averback | |
| 2015/0330195 A1 | 11/2015 | Dong et al. | |
| 2016/0215031 A1 | 7/2016 | Averback | |

FOREIGN PATENT DOCUMENTS

| | | |
|---|---|---|
| JP | 06 256 387 | 9/1994 |
| WO | WO 94/23756 | 10/1994 |
| WO | WO 98/38204 | 9/1998 |
| WO | WO 99/19347 | 4/1999 |
| WO | WO 00/34477 | 6/2000 |
| WO | WO 00/55198 | 9/2000 |
| WO | WO 00/56767 | 9/2000 |
| WO | WO 00/58339 | 10/2000 |
| WO | WO 00/58495 | 10/2000 |
| WO | WO 00/63230 | 10/2000 |
| WO | WO 01/46237 | 6/2001 |
| WO | WO 02/00718 | 1/2002 |
| WO | WO 02/34915 | 5/2002 |
| WO | WO 02/070539 | 9/2002 |
| WO | WO 02/074323 | 9/2002 |
| WO | WO 02/092115 | 11/2002 |
| WO | WO 02/097030 | 12/2002 |

OTHER PUBLICATIONS

Kunit, Research and Reports in Urology, Jun. 2014, 67-70 (Year: 2014).*
Website: https://pubchem.ncbi.nlm.nih.gov/compound/16207730#section=Top, retrived on Mar. 13, 2018 (Year: 2018).*
International Search Report PCT/IB2017/053626 dated Sep. 25, 2017.
Written Opinion of the International Searching Authority PCT/IB2017/053626 dated Sep. 25, 2017.
Paul Averback, "Nymox Announces Prostate Cancer Clinical Trial Results from Completed 18 Month Endpoint Study", Feb. 9, 2016, XP055404013 URL:http://money.cnn.com/news/newsfeeds/articles/globewswire/6174512.htm.
Paul Averback, "Nymox Announces New Prostate Cancer Clinical Trial Results: Significantly Better Clinical Outcomes After Up to 2.8 Years for NX-1207 Phase 2 Prostate Cancer Treated Patients Compared to Control Group", Apr. 20, 2015, XP055307906 URL:http://www.nymox.com/resources/content/d235.pdf.
Paul Averback, "Nymox Reports Long-Term Prostate Cancer Results in 7 Year Prospective Study of 995 U.S. Middle-Aged and Elderly Men Without Cancer Study Shows Major Reduction to Cumulative Incidence of Prostate Cancer in Study to 1.3%", Jun. 22, 2016, XP055404136 URL:http://www.nymox.com/resources/content/d262.pdf.
Anonymous, "Prostate-Specific Antigen (PSA) Test—National Cancer Institute", May 5, 2017, XP055404170 URL:https://www.cancer.gov/types/prostate/psa-fact-sheet.
Paul Averback, U.S. Appl. No. 14/808,731, filed Jul. 24, 2015.
Paul Averback, U.S. Appl. No. 14/738,551, filed Jun. 12, 2015.
De La Monte Suzanne M. et al.: "Characterization of the AD7C-NTP cDNA Expression in Alzheimer's Disease and Measurement of a 41-kD Protein in Cerebrospinal Fluid" Journal of Clinical Investigation, vol. 100, No. 12, Dec. 1997, pp. 3093-3104.
Golubnitschaja-Labudova et al: "Altered gene expression in lymphocytes of patients with normal-tension glaucoma"; Current Eye Research, vol. 21, No. 5, 2000, pp. 867-876.

(Continued)

*Primary Examiner* — Satyanarayana R Gudibande
(74) *Attorney, Agent, or Firm* — Pillsbury Winthrop Shaw Pittman LLP

(57) ABSTRACT

The embodiments include methods of preventing or reducing the progression of prostate cancer in mammals susceptible to developing prostate cancer, and to methods of reducing the incidence of clinically detected prostate cancer, using compositions containing compounds based on small peptides and a pharmaceutically acceptable carrier. The method includes, but is not limited to, administering the compounds intramuscularly, orally, intravenously, intraprostatically, intrathecally, intratumorally, intranasally, topically, transdermally, etc., either alone or conjugated to a carrier to a mammal in need thereof.

14 Claims, No Drawings
Specification includes a Sequence Listing.

(56) References Cited

OTHER PUBLICATIONS

De Reggi et al.: "The glycan moiety of human pancreatic lithostathine", European Journal of Biochemistry, vol. 230, 1995, pp. 503-510.
Lasserre et al.: "A Novel Gene (HIP) Activated in Human Primary Liver Cancer" Cancer Research, vol. 52, Sep. 15, 1992, pp. 5089-5095.
Raychowdhury et al., "Alternative splicing produces a divergent cytoplasmic tail in the human endothelial thromboxane A2 Receptor"; J, Bio. Chem., 1994, vol. 269, No. 30, pp. 19256-19261.
Gene Accession No. XM_032307, pp. 1-2.
Skolnick et al., "From genes to protein structure and function: novel applications of computational approaches in the genomic era", Trends in Biotech. vol. 18: pp. 34-39, Jan. 2000.
Ngo et al., In "The Protein Folding Problem and Tediary Structure Prediction", Chapter 14:Computational Complexity Protein Structure Prediction, and the Levinthal Paradox, 1994, Merz, et al. (ed.), Birkhauser, Boston, MA, pp. 433, and pp. 491-495.
Burgess, et al. "Possible dissociation of the heparin-binding and mitogenic activities of heparin-binding (acidic fibroblast) growth factor-1 from its receptor-binding activities by site-directed mutagenesis of a single bysine residue", J. Cell Biol. 111: 2129-2138, 1990.
Lazar, et al. "Transforming growth factor: mutation of aspartic acid 47 and leucine 48 results in different biological activities"; Mol. Cell. Biol., vol. 8, No. 3; pp. 1247-1252, Mar. 1988.
Bowie et al, "Deciphering the Message in Protein Sequences: Tolerance to Amino Acid Substitutions"; Science, vol. 247: pp. 1306-1310; Mar. 16, 1990.
International Search Report for PCT/CA02/01757 dated Oct. 8, 2003.
Okada et al, "Molecular and functional characterization of a novel mouse transient receptor potential protein homologue TRP7", 1999, vol. 274, No. 39, pp. 27359-27370.
Nair et al., "Mimicry of native peptide antigens by the corresponding retro-inverso analogs is dependent on their intrinsic structure and interaction propensities", 2003, pp. 1362-1373.

Bork; "Powers and Pitfalls in Sequence Analysis: The 70% Hurdle." Genome Research, 2000; pp. 398-400.
Smith et al., "The challenges of genome sequence annotation or The devil is in the details", Nature Biotechnology vol. 15; pp. 1222-1223, Nov. 1997.
Doerks et al., "Protein annotation: detective work for function prediction." Trends in Genetics, vol. 14, No. 6, pp. 248-250, Jun. 1998.
Bork and Bairoch; "Go hunting in sequence databases but watch out for the traps." Trends in Genetics, vol. 12, No. 10, pp. 425-427, Oct. 1996.
Wen et al. "PTEN controls tumor-induced angiogenesis", Proc. Nat. Acad. Sci. U.S.A., vol. 98, No. 8, pp. 4622-4627, Apr. 2001.
Brady et al. "Reflections on a peptide", Nature, Apr. 21, 1994; vol. 368, pp. 692-693.
Feltkamp et al.: "Efficient MHC Class I-Peptide Binding is Required Bu Does Not Ensure MHC Class I-Restricted Immunogenicity"; Molecular Immunology, vol. 31, No. 18, Dec. 1994, pp. 1391-1401.
Sijts et al.: "Immunodominant Mink Cell Focus-Inducing Murine Leukemia Virus (MuLV)-Encoded CTL Epitope, Identified by its MHC Class I-Binding Motif, Explains MuLV-Type Specificity of MCF-Directed Cytotoxic T Lymphocytes", Journal of Immunology, vol. 152, 1994, pp. 106-116.
International Search Report issued in PCT/CA02/01106 dated Sep. 11, 2003.
Brenner; "Errors in genome annotation." Apr. 1999, Trends in Genetics vol. 15; No. 4, pp. 132-133.
PCT International Search Report for PCT/CA02/01105, dated Sep. 30, 2003.
Database WPI: Derwent Publications Ltd., London, GB; AN 2001-530465 XP002241203 & CN 1 300 783 (Shengyuan Gene Dev Co Ltd. Shanghai) Jun. 27, 2001, abstract.
De la Monte et al.; "Modulation of neuronal thread protein expression with neuritic sprouting: relevance to Alzheimer's disease", Journal of Neurological Sciences, 138 (1-2), pp. 26-35.

\* cited by examiner

METHOD OF PREVENTING OR REDUCING THE PROGRESSION OF PROSTATE CANCER

SEQUENCE LISTING

The instant application contains a Sequence Listing which has been submitted electronically in ASCII format and is hereby incorporated by reference in its entirety. Said ASCII copy, created on Jul. 27, 2016, is named 063307-0447523_SL.txt and is 33,218 bytes in size.

BACKGROUND

1. Field of the Embodiments

The embodiments include methods of preventing or reducing the progression of prostate cancer in mammals susceptible to developing prostate cancer, and to methods of reducing the incidence of clinically detected prostate cancer, using compositions containing compounds based on small peptides and a pharmaceutically acceptable carrier. The methods include, but are not limited to, administering the compositions intramuscularly, orally, intravenously, intraperitoneally, intraprostatically, intracerebrally (intraparenchymally), intracerebroventricularly, intralesionally, intraocularly, intraarterially, intrathecally, intratumorally, intranasally, topically, transdermally, subcutaneously, or intradermally to patients in need thereof, wherein those patients who do not already have clinically detected prostate cancer are less likely to develop clinical prostate cancer, (i.e., the incidence of prostate cancer is reduced), and/or those patients who have a risk of developing prostate cancer (test-detected prostate cancer), do not exhibit substantial progression of the cancer (i.e., prevent or reduce the progression of prostate cancer).

2. Description of Related Art

The essence of many medical treatments and procedures involves the removal or destruction of harmful or unwanted tissue. Examples of such treatments include the surgical removal of cancerous or pre-cancerous growths, the destruction of metastastic tumors through chemotherapy, and the reduction of glandular (e.g. prostate) hyperplasia. Other examples include the removal of unwanted facial hair, the removal of warts, and the removal of unwanted fatty tissue.

There is a need for an effective composition that will destroy and hence either facilitate the removal of or inhibit the further growth of harmful or unwanted cells and tissue but will have mainly local effects and minimal or absent systemic toxicity. There also is a need to reduce the need for invasive surgical intervention, even after treatment with an effective composition.

Some agents known to have the ability to destroy and hence either facilitate the removal of or inhibit the further growth of harmful or unwanted cells and tissue are disclosed in U.S. patent application Ser. No. 14/808,713, filed Jul. 24, 2015, entitled: METHODS OF REDUCING THE NEED FOR SURGERY IN PATIENTS SUFFERING FROM BENIGN PROSTATIC HYPERPLASIA; U.S. patent application Ser. No. 14/606,683, filed Jan. 27, 2015, entitled: METHOD OF TREATING DISORDERS REQUIRING DESTRUCTION OR REMOVAL OF CELLS, U.S. application Ser. No. 14/738,551, filed Jun. 12, 2015, entitled: COMBINATION COMPOSITIONS FOR TREATING DISORDERS REQUIRING REMOVAL OR DESTRUCTION OF UNWANTED CELLULAR PROLIFERATIONS, U.S. patent application Publication Nos. 2007/0237780 (now abandoned); 2003/0054990 (now U.S. Pat. No. 7,172,893); 2003/0096350 (now U.S. Pat. No. 6,924,266); 2003/0096756 (now U.S. Pat. No. 7,192,929); 2003/0109437 (now U.S. Pat. No. 7,241,738); 2003/0166569 (now U.S. Pat. No. 7,317,077); 2005/0032704 (now U.S. Pat. No. 7,408,021); and 2015/0148303 (now U.S. Pat. No. 9,243,035), the disclosures of each of which are incorporated by reference herein in their entirety.

Cancer is an abnormality in a cell's internal regulatory mechanisms that results in uncontrolled growth and reproduction of the cell. Normal cells make up tissues, and when these cells lose their ability to behave as a specified, controlled, and coordinated unit, (dedifferentiation), the defect leads to disarray amongst the cell population. When this occurs, a tumor is formed.

Benign overgrowths of tissue are abnormalities in which it is desirable to remove cells from an organism. Benign tumors are cellular proliferations that do not metastasize throughout the body but do, however, cause disease symptoms. Such tumors can be lethal if they are located in inaccessible areas in organs such as the brain. There are benign tumors of organs including lung, brain, skin, pituitary, thyroid, adrenal cortex and medulla, ovary, uterus, testis, connective tissue, muscle, intestines, ear, nose, throat, tonsils, mouth, liver, gall bladder, pancreas, prostate, heart, and other organs.

Surgery often is the first step in the treatment of cancer. The objective of surgery varies. Sometimes it is used to remove as much of the evident tumor as possible, or at least to "debulk" it (remove the major bulk(s) of tumor so that there is less that needs to be treated by other means). Depending on the cancer type and location, surgery may also provide some symptomatic relief to the patient. For instance, if a surgeon can remove a large portion of an expanding brain tumor, the pressure inside the skull will decrease, leading to improvement in the patient's symptoms.

Not all tumors are amenable to surgery. Some may be located in parts of the body that make them impossible to completely remove. Examples of these would be tumors in the brainstem (a part of the brain that controls breathing) or a tumor which has grown in and around a major blood vessel. In these cases, the role of surgery is limited due to the high risk associated with tumor removal.

In some cases, surgery is not used to debulk tumor tissue because it is simply not necessary. An example is Hodgkin's lymphoma, a cancer of the lymph nodes that responds very well to combinations of chemotherapy and radiation therapy. In Hodgkin's lymphoma, surgery is rarely needed to achieve cure, but almost always used to establish a diagnosis.

Chemotherapy is another common form of cancer treatment. Essentially, it involves the use of medications (usually given by mouth or injection) which specifically attack rapidly dividing cells (such as those found in a tumor) throughout the body. This makes chemotherapy useful in treating cancers that have already metastasized, as well as tumors that have a high chance of spreading through the blood and lymphatic systems but are not evident beyond the primary tumor. Chemotherapy may also be used to enhance the response of localized tumors to surgery and radiation therapy. This is the case, for example, for some cancers of the head and neck.

Unfortunately, other cells in the human body that also normally divide rapidly (such as the lining of the stomach and hair) also are affected by chemotherapy. For this reason, many chemotherapy agents induce undesirable side effects such as nausea, vomiting, anemia, hair loss or other symptoms. These side effects are temporary, and there exist medications that can help alleviate many of these side effects. As our knowledge has continued to grow, researchers have devised newer chemotherapeutic agents that are not only better at killing cancer cells, but that also have fewer side effects for the patient.

Chemotherapy is administered to patients in a variety of ways. Some include pills and others are administered by an intravenous or other injection. For injectable chemotherapy, a patient goes to the doctor's office or hospital for treatment. Other chemotherapeutic agents require continuous infusion into the bloodstream, 24 hours a day. For these types of chemotherapy, a minor surgical procedure is performed to implant a small pump worn by the patient. The pump then slowly administers the medication. In many cases, a permanent port is placed in a patient's vein to eliminate the requirement of repeated needle sticks.

Benign tumors and malformations also can be treated by a variety of methods including surgery, radiotherapy, drug therapy, thermal or electric ablation, cryotherapy, and others. Although benign tumors do not metastasize, they can grow large and they can recur. Surgical extirpation of benign tumors has all the difficulties and side effects of surgery in general and oftentimes must be repeatedly performed for some benign tumors, such as for pituitary adenomas, meningeomas of the brain, prostatic hyperplasia, and others. In addition, some patients who receive non-surgical treatment to ameliorate the symptoms caused by benign tumors, still require subsequent invasive surgical intervention. Lepor, "Medical Treatment of Benign Prostatic Hyperplasia," Reviews in Urology, Vol. 13, No. 1, pp. 20-33 (2011), discloses a variety of studies of the efficacy of drug therapies in treating BPH, and the need for subsequent invasive surgical treatment.

The role of androgens in the development of benign prostatic hyperplasia in men is well documented (Wilson, N. Engl. J. Med. 317: 628-629, 1987). In fact, benign prostatic hyperplasia does not develop in the absence of the testes (referred to in Wendel et al., J. Urol. 108: 116-119, 1972).

Blockade of testicular androgen secretion by surgical or medical (LHRH agonist) castration is known to decrease prostatic size (Auclair et al., Biochem. Biophys. Res. Commun. 76: 855-862, 1977; Auclair et al., Endocrinology 101: 1890-1893, 1977; Labrie et al., Int. J. Andrology, suppl. 2 (V. Hansson, ed.), Scriptor Publisher APR, pp. 303-318, 1978; Labrie et al., J. Andrology 1: 209-228, 1980; Tremblay and Belanger, Contraception 30: 483-497, 1984; Tremblay et al., Contraception 30: 585-598, 1984; Dube et al., Acta Endocrinol. (Copenh) 116: 413-417, 1987; Lacoste et al., Mol. Cell. Endocrinol. 56: 141-147, 1988; White, Ann. Surg. 22: 1-80, 1895; Faure et al., Fertil. Steril. 37: 416-424, 1982; Labrie et al., Endocrine Reviews 7: 67-74, 1986; Huggins and Stevens, J. Urol. 43: 705-714, 1940; Wendel et al., J. Urol. 108: 116-119, 1972; Peters and Walsh, N. Engl. J. Med. 317: 599-604, 1987; Gabrilove et al., J. Clin. Endocrinol. Metab. 64: 1331-1333, 1987).

Several studies have shown that treatment with an antiandrogen also decreases prostatic size (Neri et al., Endocrinology, 82: 311-317, 1968; Neri et al., Investigative Urology, 10: 123-130, 1972; Tunn et al., Acta Endocrinol. (Copenh.) 91: 373-384, 1979; Seguin et al., Mol. Cell. Endocrinol., 21: 37-41, 1981; Lefebvre et al., The Prostate 3: 569-578, 1982; Marchetti and Labrie, J. Steroid Biochem, 29: 691-698, 1988; Lacoste et al., Mol. Cell. Endocrinol. 56: 141-147, 1988; Tunn et al., Invest. Urol. 18: 289-292, 1980; Scott and Wade, J. Urol. 101: 81-85, 1969; Caine et al., J. Urol. 114: 564-568, 1975; Stone et al., J. Urol. 141: 240A, 1989; Clejan et al., J. Urol. 141: 534A, 1989).

U.S. Pat. No. 3,423,507 discloses the use of the antiandrogen cyproterone acetate (1α, 2β-methylene-6-chloro-17α-acetoxy-6-dehydroprogesterone) for the treatment of benign prostatic hyperplasia. Pure antiandrogens (U.S. Pat. No. 4,329,364) cause an increase in testosterone secretion, which can result in a higher degree of aromatization into estrogens, a situation expected from current knowledge to have negative effects on prostatic hyperplasia (Jacobi et al., Endocrinology 102: 1748-1755, 1978). Several studies have shown that treatment with the combination of chemical castration (LHRH agonist) and an antiandrogen cause greater inhibition of prostatic size than either treatment used alone (Seguin et al., Mol. Cell. Endocrinol. 21: 37-41, 1981; Lefebvre et al., The Prostate 3: 569-578, 1982; Marchetti and Labrie, J. Steroid Biochem. 29: 691-698, 1988.

In the prostate as well as in many other tissues, testosterone is irreversibly converted by 5α-reductase into the more potent androgen dihydrotestosterone (Bruchovsky and Wilson, J. Biol. Chem. 243: 2012-2021, 1968; Wilson, Handbook of Physiology 5 (section 7), pp. 491-508, 1975). Inhibitors of 5 α-reductase have been found to inhibit prostatic growth (Brooks et al., Endocrinology 109: 830, 1981; Brooks et al., Proc. Soc. Exp. Biol. Med. 169: 67, 1982; Brooks et al., Prostate 3: 35, 1982; Wenderoth et al., Endocrinology 113, 569-573, 1983; McConnell et al., J. Urol. 141: 239A, 1989); Stoner, E., Lecture on the role of 5.alpha.-reductase inhibitor in benign prostatic hypertropy, 84th AUA Annual Meeting, Dallas, May 8, 1989.

The inhibitory effect of the 5 α-reductase inhibitor Merck L 652,931 on prostatic and seminal vesicle development in the prepubertal rat was described in Proc. 71st Annual Meeting of Endocr. Soc. abst. #1165, p. 314, 1989. The inhibitory effect of MK-906 on dihydrotestosterone formation in men has been described in men by Gormley et al., in Proc. 71st Annual Meeting of Endocr. Soc., abst. #1225, p. 329, 1989; Imperato-McGinley et al., in Proc. 71st Annual Meeting of Endocr. Soc., abst. #1639, p. 432, 1989; Geller and Franson, in Proc. 71st Annual Meeting of Endocr. Soc., abst. #1640, p. 432, 1989 and Tenover et al., in Proc. 71st Annual Meeting of Endocr. Soc., abst. #583, p. 169, 1989. The activity of the 5 α-reductase inhibitors N,N-diethyl-4-methyl-3-oxo-4-aza-5.alpha.-androstane-17.beta.-carboxamide (4-MA) and 6-methylene-4-pregnene-3,20-dione (LY 207320) has been described by Toomey et al., Proc. 71st Annual Meeting of Endocr. Soc., abst. #1226, p. 329, 1989.

In addition to the well-known effect of androgens on prostatic growth, there are many studies which show that estrogens play also a role in proliferation of the prostate (Walsh and Wilson, J. Clin. Invest. 57: 1093-1097, 1976; Robinette et al., Invest. Urol. 15: 425-432, 1978; Moore et al., J. Clin. Invest. 63: 351-257, 1979). Moreover, estrogens have been shown to enhance androgen-induced prostatic growth in the dog (Walsh and Wilson, J. Clin. Invest. 57: 1093-1097, 1976; Jacobi et al., Endocrinology 102: 1748-1755, 1978; Tunn et al., Urol. Int. 35: 125-140, 1980). A possible explanation of this enhancing effect of estrogen on androgen-induced prostate growth, is the observation that 17β-estradiol has been shown to increase androgen binding in the dog prostate (Moore et al., J. Clin. Invest. 63: 351-357, 1979).

The antiestrogen Tamoxifen has been shown to improve steroid-induced benign prostatic hyperplasia in the dog (Funke et al., Acta Endocrinol. 100: 462-472, 1982). Administration of the antiestrogen Tamoxifen in association with the steroidal antiandrogen cyproterone acetate in patients suffering from benign prostatic hyperplasia showed beneficial effects on the symptoms of the disease (Di Silverio et al., in Ipertrofia Prostatica Benigna (F. Di Silverio, F. Neumann and M. Tannenbaum, eds), Excerpta Medica, pp. 117-125, 1986). In U.S. Pat. No. 4,310,523, it is proposed that a combination of an antiandrogen and an antiestrogen is effective for the prophylaxis and/or therapy of benign prostatic hyperplasia. Tamoxifen, however, has intrinsic estrogenic activity which limits its effectiveness.

Estrogen formation resulting from aromatization of androgens, occurs at several sites. In the male, aromatization of androgens has been demonstrated in the testis, adipose and muscle tissue, skin, liver, brain and prostate (Schweikert et al., J. Clin. Endocrinol. Metab. 40: 413-417, 1975; Folker and James, J. Steroid Biochem. 49: 687-690, 1983; Longcope et al., J. Clin. Endocrinol. Metab. 46: 146-152, 1978; Lacoste and Labrie, unpublished data; Stone et al., The Prostate 9: 311-318, 1986; Stone et al., Urol. Res. 15: 165-167, 1987). There is evidence for an increased production of estrogens in the prostatic tissue of benign prostatic hyperplasia patients (Stone et al., The Prostate 9: 311-318, 1986). Such data indicate that the local formation of estrogens may play a crucial role in stimulating prostatic growth in excess of the action predicted by circulating estrogens.

U.S. Pat. No. 4,472,382 discloses treatment of BPH with an antiandrogen and certain peptides which act as LH-RH agonists. U.S. Pat. No. 4,596,797 discloses aromatase inhibitors as a method of prophylaxis and/or treatment of prostatic hyperplasia. U.S. Pat. No. 4,760,053 describes a treatment of certain cancers which combines an LHRH agonist with an antiandrogen and/or an antiestrogen and/or at least one inhibitor of sex steroid biosynthesis. U.S. Pat. No. 4,775,660 discloses a method of treating breast cancer with a combination therapy which may include surgical or chemical prevention of ovarian secretions and administering an antiandrogen and an antiestrogen.

U.S. Pat. No. 4,659,695 discloses a method of treatment of prostate cancer in susceptible male animals including humans whose testicular hormonal secretions are blocked by surgical or chemical means, e.g. by use of an LHRH agonist, which comprises administering an antiandrogen, e.g. flutamide, in association with at least one inhibitor of sex steroid biosynthesis, e.g. aminoglutethimide and/or ketoconazole. The disclosures of each of the above-mentioned patents (U.S. Pat. Nos. 4,472,382, 4,596,797, 4,760,053, 4,775,660, and 4,659,695) are incorporated by reference herein in their entireties.

BPH is caused by increased activity of both androgens and estrogens. Because of such a dual etiology of BPH, proposed hormonal therapies have been less than satisfactory and have all been unpredictable while, frequently, causing unacceptable side-effects. Moreover, the prior art treatment seldomly resulted in a decrease in prostatic volume above about 20 to 30% with inconsistent effects on the symptomatology (Scott and Wade, J. Urol. 101: 81-85, 1969; Caine et al., J. Urol. 114: 564-568, 1975; Peters and Walsh, New Engl. J. Med. 317: 599-604, 1987; Gabrilove et al., J. Clin. Endocrinol. Metab. 64: 1331-1333, 1987; Stone et al., J. Urol. 141: 240A, 1989; Clejan et al., J. Urol. 141: 534A, 1989; Stoner, E., Lecture on the role of 5 α-reductase inhibitor in benign prostatic hypertrophy, 84th AUA Annual Meeting, Dallas, May 8, 1989.

The elucidation of the mechanism summarized above has resulted in the recent development of effective agents to control, and in many cases reverse, the advance of BPH. In the forefront of these agents is Merck & Co., Inc.s' product PROSCAR® (finasteride). The effect of this compound is to inhibit the enzyme testosterone 5α reductase, which converts testosterone into 5α-dihydrotesterone, resulting in a reduced rate of prostatic enlargement, and often reduction in prostatic mass.

Prostate cancer is known as a disease with an extremely high prevalence relative to its clinical incidence in the population. Prostate cancer has a high asymptomatic incidence and a long asymptomatic duration. Prostate cancer has an interval of 7 to 14 years on average during which the cancer is present but is preclinical because it is not detected by typical clinical or laboratory examinations (see Etzioni, R et al., Am J Epidemiol. Vol. 148, pp. 775-85 (1998); and Gulati, R, et al., Cancer Epidemiol Biomarkers Prev; Vol. 20(5), pp. 740-50 (2011)). These preclinical asymptomatic prostate cancers prior to their overt diagnosis are a reasonable target for treatment which can benefit patients before the cancers have become clinically apparent or detected otherwise.

In all or most of these instances, there is a need for treatments that can remove or destroy the unwanted cellular elements without the risks and side effects of conventional therapies, or treatments that can remove the unwanted cellular elements with more precision. There also is a need to develop therapies that can prevent or reduce the progression of prostate cancer, or reduce the incidence of clinically detected prostate cancer.

Throughout this description, including the foregoing description of related art, any and all publicly available documents described herein, including any and all U.S. patent published patent applications, are specifically incorporated by reference herein in their entirety. The foregoing description of related art is not intended in any way as an admission that any of the documents described therein, including pending U.S. patent applications, are prior art to the present disclosure. Moreover, the description herein of any disadvantages associated with the described products, methods, and/or apparatus, is not intended to limit the embodiments. Indeed, aspects of the embodiments may include certain features of the described products, methods, and/or apparatus without suffering from their described disadvantages.

SUMMARY OF THE EMBODIMENTS

There remains a need in the art for new, less toxic, and less frequent (e.g., avoiding the need to take medications daily or weekly) treatments for preventing or reducing the progression or incidence of prostate cancer. There also remains a need in the art for such treatments that reduce the incidence of clinically detected prostate cancer. The embodiments satisfy these needs.

This disclosure is premised in part on the discovery that certain NTP peptides, including a specific peptide described by the amino acid sequence Ile-Asp-Gln-Gln-Val-Leu-Ser-Arg-Ile-Lys-Leu-Glu-Ile-Lys-Arg-Cys-Leu (SEQ ID NO: 66), are capable of preventing or reduce the progression of prostate cancer, as well as reducing the incidence of clinically detected prostate cancer.

This disclosure also is premised in part on the discovery that certain NTP peptides, including a specific peptide described by the amino acid sequence Ile-Asp-Gln-Gln-Val-Leu-Ser-Arg-Ile-Lys-Leu-Glu-Ile-Lys-Arg-Cys-Leu (SEQ ID NO: 66), either alone or in combination with an additional active agent capable of treating and/or killing unwanted cellular proliferations in mammals, provide an unexpected improvement in patients suffering from or susceptible to developing prostate cancer.

Some embodiments are directed to methods of preventing or reducing the progression of prostate cancer in mammals comprising administering to a mammal in need thereof a therapeutically effective amount of a composition comprising an NTP peptide, either alone or in combination with at least one additional active agent capable of treating and/or killing unwanted cellular proliferations in mammals. In an embodiment, there are provided methods of reducing the incidence of prostate cancer in mammals comprising administering to a mammal in need thereof a therapeutically effective amount of a composition comprising an NTP peptide, either alone or in combination with at least one additional active agent capable of treating and/or killing unwanted cellular proliferations in mammals.

The compositions can be administered intramuscularly, orally, intravenously, intraperitoneally, intracerebrally (intraparenchymally), intracerebroventricularly, intratumorally, intralesionally, intradermally, intrathecally, intranasally, intraocularly, intraarterially, topically, transdermally, via an aerosol, infusion, bolus injection, implantation device, sustained release system etc. Alternatively, the NTP peptides can be expressed in vivo by administering a gene that expresses the NTP peptides, by administering a vaccine that induces such production or by introducing cells, bacteria or viruses that express the peptide in vivo, because of genetic modification or otherwise.

In another embodiment, administering a composition comprising an NTP peptide, either alone or in combination with at least one additional active agent capable of treating and/or killing unwanted cellular proliferations in mammals reduces the incidence of clinically detected prostate cancer by more than 15%, when compared to the known expected incidence of clinically detected prostate cancer.

Both the foregoing general description and the following detailed description are exemplary and explanatory and are intended to provide further explanation of the embodiments as claimed. Other objects, advantages, and features will be readily apparent to those skilled in the art from the following detailed description of the embodiments.

DETAILED DESCRIPTION OF THE PREFERRED EMBODIMENTS

Before the present proteins, nucleotide sequences, peptides, compositions, active agents, etc., and methods are described, it is understood that this invention is not limited to the particular methodology, protocols, cell lines, vectors, and reagents described, as these may vary. It also is to be understood that the terminology used herein is for the purpose of describing particular embodiments only, and is not intended to limit the scope of the present embodiments which will be limited only by the appended claims.

Terms and phrases used herein are defined as set forth below unless otherwise specified. Throughout this description, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Amino acids and amino acid residues described herein may be referred to according to the accepted one or three-letter code provided in the table below.

TABLE 1

| Three-Letter Amino Acid | One-Letter Symbol | Symbol |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

The expression "NTP peptide" refers to peptides comprising amino acid sequences corresponding to at least a part of the amino acid sequence of Neural Thread Proteins or to fragments of Neural Thread Proteins and includes homologues, derivatives, variants, fusion proteins, and peptide mimetics of such peptides unless the context indicates otherwise. The expression "NTP peptide" also refers to a peptide or other composition of matter claimed in one or more of the following U.S. patent application Publication Nos. 2007/0237780 (now abandoned); 2003/0054990 (now U.S. Pat. No. 7,172,893); 2003/0096350 (now U.S. Pat. No. 6,924,266); 2003/0096756 (now U.S. Pat. No. 7,192,929); 2003/0109437 (now U.S. Pat. No. 7,241,738); 2003/0166569 (now U.S. Pat. No. 7,317,077); and 2005/0032704 (now U.S. Pat. No. 7,408,021). The disclosures of each of these applications are incorporated by reference herein in their entirety. Specific peptides are listed below.

1) SEQ ID NO. 1:
MEFSLLLPRLECNGA
or

Met-Glu-Phe-Ser-Leu-Leu-Leu-Pro-Arg-Leu-Glu-Cys-Asn-Gly-Ala

2) SEQ ID NO. 2:
GAISAHRNLRLPGSS
or

Gly-Ala-Ile-Ser-Ala-His-Arg-Asn-Leu-Arg-Leu-Pro-Gly-Ser-Ser

3) SEQ ID NO. 3:
DSPASASPVAGITGMCT
or

Asp-Ser-Pro-Ala-Ser-Ala-Ser-Pro-Val-Ala-Gly-Ile-Thr-Gly-Met-Cys-Thr

4) SEQ ID NO. 4:
MCTHARLILYFFLVEM
or

Met-Cys-Thr-His-Ala-Arg-Leu-Ile-Leu-Tyr-Phe-Phe-Leu-Val-Glu-Met

5) SEQ ID NO. 5:
YFFLVEMEFLH
or

Tyr-Phe-Phe-Leu-Val-Glu-Met-Glu-Phe-Leu-His

-continued

6) SEQ ID NO. 6:
VGQAGLELPTS
or

Val-Gly-Gln-Ala-Gly-Leu-Glu-Leu-Pro-Thr-Ser

7) SEQ ID NO. 7:
DDPSVSASQSARYRTGH
or

Asp-Asp-Pro-Ser-Val-Ser-Ala-Ser-Gln-Ser-Ala-
Arg-Tyr-Arg-Thr-Gly-His

8) SEQ ID NO. 8:
TGHHARLCLANFCG
or

Thr-Gly-His-His-Ala-Arg-Leu-Cys-Leu-Ala-Asn-
Phe-Cys-Gly

9) SEQ ID NO. 9:
ANFCGRNRVSLMCPSWS
or

Ala-Asn-Phe-Cys-Gly-Arg-Asn-Arg-Val-Ser-Leu-
Met-Cys-Pro-Ser-Trp-Ser

10) SEQ ID NO. 10:
PELKQSTCLSLPKCWDYRR
or

Pro-Glu-Leu-Lys-Gln-Ser-Thr-Cys-Leu-Ser-Leu-
Pro-Lys-Cys-Trp-Asp-Tyr-Arg-Arg

11) SEQ ID NO. 11:
LKQSTCLSLPKCWDYRR
or

Leu-Lys-Gln-Ser-Thr-Cys-Leu-Ser-Leu-Pro-Lys-
Cys-Trp-Asp-Tyr-Arg-Arg

12) SEQ ID NO. 12:
STCLSLPKCWDYRR
or

Ser-Thr-Cys-Leu-Ser-Leu-Pro-Lys-Cys-Trp-Asp-
Tyr-Arg-Arg

13) SEQ ID NO. 13:
LSLPKCWDYRR
or

Leu-Ser-Leu-Pro-Lys-Cys-Trp-Asp-Tyr-Arg-Arg

14) SEQ ID NO. 14:
KCWDYRRAAVPGL
or

Lys-Cys-Trp-Asp-Tyr-Arg-Arg-Ala-Ala-Val-Pro-Gly-
Leu

15) SEQ ID NO. 15:
KCWDYRRAAVPGLFILFFL
or

Lys-Cys-Trp-Asp-Tyr-Arg-Arg-Ala-Ala-Val-Pro-Gly-
Leu-Phe-Ile-Leu-Phe-Phe-Leu

16) SEQ ID NO. 16:
KCWDYRRAAVPGLFILFFLRHRCP
or

Lys-Cys-Trp-Asp-Tyr-Arg-Arg-Ala-Ala-Val-Pro-Gly-
Leu-Phe-Ile-Leu-Phe-Phe-Leu-Arg-His-Arg-Cys-Pro

17) SEQ ID NO. 17:
KCWDYRRAAVPGLFILFFLRHRCPTLTQDEVQWCDHSS
or

-continued

Lys-Cys-Trp-Asp-Tyr-Arg-Arg-Ala-Ala-Val-Pro-Gly-
Leu-Phe-Ile-Leu-Phe-Phe-Leu-Arg-His-Arg-Cys-Pro-
Thr-Leu-Thr-Gln-Asp-Glu-Val-Gln-Trp-Cys-Asp-His-
Ser-Ser

18) SEQ ID NO. 18:
WDYRR
or

Trp-Asp-Tyr-Arg-Arg

19) SEQ ID NO. 19:
FILFFLRHRCPTL
or

Phe-Ile-Leu-Phe-Phe-Leu-Arg-His-Arg-Cys-Pro-Thr-
Leu

20) SEQ ID NO. 20:
FILFFLRHRCPTLTQDEVQWCDHSS
or

Phe-Ile-Leu-Phe-Phe-Leu-Arg-His-Arg-Cys-Pro-Thr-
Leu-Thr-Gln-Asp-Glu-Val-Gln-Trp-Cys-Asp-His-Ser-
Ser

21) SEQ ID NO. 21:
HRCPTLTQDEVQWCDHSSLQPSTPEIKHP
or

His-Arg-Cys-Pro-Thr-Leu-Thr-Gln-Asp-Glu-Val-Gln-
Trp-Cys-Asp-His-Ser-Ser-Leu-Gln-Pro-Ser-Thr-Pro-
Glu-Ile-Lys-His-Pro

22) SEQ ID NO. 22:
PASASQVAGTKDMH
or

Pro-Ala-Ser-Ala-Ser-Gln-Val-Ala-Gly-Thr-Lys-Asp-
Met-His

23) SEQ ID NO. 23:
DMHHYTWLIFIFIFNFLR
or

Asp-Met-His-His-Tyr-Thr-Trp-Leu-Ile-Phe-Ile-Phe-
Ile-Phe-Asn-Phe-Leu-Arg

24) SEQ ID NO. 24:
HYTWLIFIFIFNFLRQSLN
or

His-Tyr-Thr-Trp-Leu-ILe-Phe-Ile-Phe-Ile-Phe-Asn-
Phe-Leu-Arg-Gln-Ser-Leu-Asn

25) SEQ ID NO. 25:
SVTQAGVQWRNLGSLQPLPPGFKLFSCPSLLSSWDYRRPPRLANF
or

Ser-Val-Thr-Gln-Ala-Gly-Val-Gln-Trp-Arg-Asn-Leu-
Gly-Ser-Leu-Gln-Pro-Leu-Pro-Pro-Gly-Phe-Lys-Leu-
Phe-Ser-Cys-Pro-Ser-Leu-Leu-Ser-Ser-Trp-Asp-Tyr-
Arg-Arg-Pro-Pro-Arg-Leu-Ala-Asn-Phe

26) SEQ ID NO. 26:
PGFKLFSCPSLLSSWDYRR
or

Pro-Gly-Phe-Lys-Leu-Phe-Ser-Cys-Pro-Ser-Leu-Leu-
Ser-Ser-Trp-Asp-Tyr-Arg-Arg

27) SEQ ID NO. 27:
FKLFSCPSLLSSWDYRRPPRLANF
or

Phe-Lys-Leu-Phe-Ser-Cys-Pro-Ser-Leu-Leu-Ser-Ser-
Trp-Asp-Tyr-Arg-Arg-Pro-Pro-Arg-Leu-Ala-Asn-Phe

28) SEQ ID NO. 28:
FSCPSLLSSWDYRR
or

-continued

Phe-Ser-Cys-Pro-Ser-Leu-Leu-Ser-Ser-Trp-Asp-Tyr-
Arg-Arg

29) SEQ ID NO. 29:
SLLSSWDYRR
or

Ser-Leu-Leu-Ser-Ser-Trp-Asp-Tyr-Arg-Arg

30) SEQ ID NO. 30:
SSWDY
or

Ser-Ser-Trp-Asp-Tyr

31) SEQ ID NO. 31:
SSWDYRR
or

Ser-Ser-Trp-Asp-Tyr-Arg-Arg

32) SEQ ID NO. 32:
SSWDYRRPPRLANFFVFLVEMGFTM
or

Ser-Ser-Trp-Asp-Tyr-Arg-Arg-Pro-Pro-Arg-Leu-Ala-
Asn-Phe-Phe-Val-Phe-Leu-Val-Glu-Met-Gly-Phe-Thr-
Met

33) SEQ ID NO. 33:
FVFLVEMGFTM
or

Phe-Val-Phe-Leu-Val-Glu-Met-Gly-Phe-Thr-Met

34) SEQ ID NO. 34:
MGFTMFARLILISGPCDLPASAS
or

Met-Gly-Phe-Thr-Met-Phe-Ala-Arg-Leu-Ile-Leu-Ile-
Ser-Gly-Pro-Cys-Asp-Leu-Pro-Ala-Ser-Ala-Ser

35) SEQ ID NO. 35:
ISGPC
or

Ile-Ser-Gly-Pro-Cys

36) SEQ ID NO. 36:
DLPASASQSAGITGVSH
or

Asp-Leu-Pro-Ala-Ser-Ala-Ser-Gln-Ser-Ala-Gly-Ile-
Thr-Gly-Val-Ser-His

37) SEQ ID NO. 37:
GVSHHARLIFNFCLFEM
or

Gly-Val-Ser-His-His-Ala-Arg-Leu-Ile-Phe-Asn-Phe-
Cys-Leu-Phe-Glu-Met

38) SEQ ID NO. 38:
NFCLFEMESH
or

Asn-Phe-Cys-Leu-Phe-Glu-Met-Glu-Ser-His

39) SEQ ID NO. 39:
SVTQAGVQWPNLGSLQPLPPGLKRFSCLSLPSSWDYGHLPPHPANF
or

Ser-Val-Thr-Gln-Ala-Gly-Val-Gln-Trp-Pro-Asn-Leu-
Gly-Ser-Leu-Gln-Pro-Leu-Pro-Pro-Gly-Leu-Lys-Arg-
Phe-Ser-Cys-Leu-Ser-Leu-Pro-Ser-Ser-Trp-Asp-Tyr-
Gly-His-Leu-Pro-Pro-His-Pro-Ala-Asn-Phe

40) SEQ ID NO. 40:
PPGLKRFSCLSLPSSWDYG
or

Pro-Pro-Gly-Leu-Lys-Arg-Phe-Ser-Cys-Leu-Ser-Leu-
Pro-Ser-Ser-Trp-Asp-Tyr-Gly

41) SEQ ID NO. 41:
FSCLSLPSSWDYGH
or

Phe-Ser-Cys-Leu-Ser-Leu-Pro-Ser-Ser-Trp-Asp-Tyr-
Gly-His

42) SEQ ID NO. 42:
LSLPSSWDY
or

Leu-Ser-Leu-Pro-Ser-Ser-Trp-Asp-Tyr

43) SEQ ID NO. 43:
SSWDYGHLPPHPANFCIFIRGGVSPYLSGWSQTPDLR
or

Ser-Ser-Trp-Asp-Tyr-Gly-His-Leu-Pro-Pro-His-Pro-
Ala-Asn-Phe-Cys-Ile-Phe-Ile-Arg-Gly-Gly-Val-Ser-
Pro-Tyr-Leu-Ser-Gly-Trp-Ser-Gln-Thr-Pro-Asp-Leu-
Arg

44) SEQ ID NO. 44:
PGFFKLFSCPSLLSSWDYRR
or

Pro-Gly-Phe-Phe-Lys-Leu-Phe-Ser-Cys-Pro-Ser-Leu-
Leu-Ser-Ser-Trp-Asp-Tyr-Arg-Arg

45) SEQ ID NO. 45:
PELKQSTCLSLPKCWDYRR
or

Pro-Glu-Leu-Lys-Gln-Ser-Thr-Cys-Leu-Ser-Leu-Pro-
Lys-Cys-Trp-Asp-Tyr-Arg-Arg

46) SEQ ID NO. 46:
PPGLKRFSCLSLPSSWDYG
or

Pro-Pro-Gly-Leu-Lys-Arg-Phe-Ser-Cys-Leu-Ser-Leu-
Pro-Ser-Ser-Trp-Asp-Tyr-Gly

47) SEQ ID NO. 47:
FSCLSLPSSWDYGH
or

Phe-Ser-Cys-Leu-Ser-Leu-Pro-Ser-Ser-Trp-Asp-Tyr-
Gly-His

48) SEQ ID NO. 48:
STCLSLPKCWDYRR
or

Ser-Thr-Cys-Leu-Ser-Leu-Pro-Lys-Cys-Trp-Asp-Tyr-
Arg-Arg

49) SEQ ID NO. 49:
FSCPSLLSSWDYRR
or

Phe-Ser-Cys-Pro-Ser-Leu-Leu-Ser-Ser-Trp-Asp-Tyr-
Arg-Arg

50) SEQ ID NO. 50:
LSLPSSWDY
or

Leu-Ser-Leu-Pro-Ser-Ser-Trp-Asp-Tyr

51) SEQ ID NO. 51:
LSLPKCWDYRR
or

Leu-Ser-Leu-Pro-Lys-Cys-Trp-Asp-Tyr-Arg-Arg

52) SEQ ID NO. 52:
SLLSSWDYRR
or

Ser-Leu-Leu-Ser-Ser-Trp-Asp-Tyr-Arg-Arg

53) SEQ ID NO. 53:
LPSSWDYRR
or

Leu-Pro-Ser-Ser-Trp-Asp-Tyr-Arg-Arg

54) SEQ ID NO. 54:
SSWDYRR
or

Ser-Ser-Trp-Asp-Tyr-Arg-Arg

55) SEQ ID NO. 55:
SSWDY
or

Ser-Ser-Trp-Asp-Tyr

56) SEQ ID NO. 56:
SSWDYRRFILFFL
or

Ser-Ser-Trp-Asp-Tyr-Arg-Arg-Phe-Ile-Leu-Phe-Phe-Leu

57) SEQ ID NO. 57:
WDYRRFIFNFL
or

Trp-Asp-Tyr-Arg-Arg-Phe-Ile-Phe-Asn-Phe-Leu

58) SEQ ID NO. 58:
FNFCLF
or

Phe-Asn-Phe-Cys-Leu-Phe

59) SEQ ID NO. 59:
FIFNFL
or

Phe-Ile-Phe-Asn-Phe-Leu

60) SEQ ID NO. 60:
PASASPVAGITGM
or

Pro-Ala-Ser-Ala-Ser-Pro-Val-Ala-Gly-Ile-Thr-Gly-Met

61) SEQ ID NO. 61:
PASASQVAGTKDM
or

Pro-Ala-Ser-Ala-Ser-Gln-Val-Ala-Gly-Thr-Lys-Asp-Met

62) SEQ ID NO. 62:
PASASQSAGITGV
or

Pro-Ala-Ser-Ala-Ser-Gln-Ser-Ala-Gly-Ile-Thr-Gly-Val

63) SEQ ID NO. 63:
PASASPVAG
or

Pro-Ala-Ser-Ala-Ser-Pro-Val-Ala-Gly

64) SEQ ID NO. 64:
FFLVEM
or

Phe-Phe-Leu-Val-Glu-Met

65) SEQ ID NO. 65:
SVTQAGVQW
or

Ser-Val-Thr-Gln-Ala-Gly-Val-Gln-Trp

66) SEQ ID NO. 66:
IDQQVLSRIKLEIKRCL
or

Ile-Asp-Gln-Gln-Val-Leu-Ser-Arg-Ile-Lys-Leu-Glu-Ile-Lys-Arg-Cys-Leu

67) SEQ ID NO. 67:
LSRIKLEIK
or

Leu-Ser-Arg-Ile-Lys-Leu-Glu-Ile-Lys

68) SEQ ID NO. 68:
GDHGRPNLSRLKLAIKYEVKKM
or

Gly-Asp-His-Gly-Arg-Pro-Asn-Leu-Ser-Arg-Leu-Lys-Leu-Ala-Ile-Lys-Tyr-Glu-Val-Lys-Lys-Met

69) SEQ ID NO. 69:
QQSIAVKFLAVFGVSI
or

Gln-Gln-Ser-Ile-Ala-Val-Lys-Phe-Leu-Ala-Val-Phe-Gly-Val-Ser-Ile

70) SEQ ID NO. 70:
GLLFPVFSVCYLIAPKSPLGL
or

Gly-Leu-Leu-Phe-Pro-Val-Phe-Ser-Val-Cys-Tyr-Leu-Ile-Ala-Pro-Lys-Ser-Pro-Leu-Gly-Leu

71) SEQ ID NO. 71:
MMVCWNRFGKWVYFI
or

Met-Met-Val-Cys-Trp-Asn-Arg-Phe-Gly-Lys-Trp-Val-Tyr-Phe-Ile

72) SEQ ID NO. 72:
SAIFNFGPRYLYHGV
or

Ser-Ala-Ile-Phe-Asn-Phe-Gly-Pro-Arg-Tyr-Leu-Tyr-His-Gly-Val

73) SEQ ID NO. 73:
PFYFLILVRIISFLI
or

Pro-Phe-Tyr-Phe-Leu-Ile-Leu-Val-Arg-Ile-Ile-Ser-Phe-Leu-Ile

74) SEQ ID NO. 74:
GDMEDVLLNCTLLKR
or

Gly-Asp-Met-Glu-Asp-Val-Leu-Leu-Asn-Cys-Thr-Leu-Leu-Lys-Arg

75) SEQ ID NO. 75:
SSRFRFWGALVCSMD
or

Ser-Ser-Arg-Phe-Arg-Phe-Trp-Gly-Ala-Leu-Val-Cys-Ser-Met-Asp

76) SEQ ID NO. 76:
SCRFSRVAVTYRFIT
or

-continued

Ser-Cys-Arg-Phe-Ser-Arg-Val-Ala-Val-Thr-Tyr-Arg-Phe-Ile-Thr

77) SEQ ID NO. 77:
LLNIPSPAVWMARNT
or

Leu-Leu-Asn-Ile-Pro-Ser-Pro-Ala-Val-Trp-Met-Ala-Arg-Asn-Thr

78) SEQ ID NO. 78:
MAQSRLTATSASRVQ
or

Met-Ala-Gln-Ser-Arg-Leu-Thr-Ala-Thr-Ser-Ala-Ser-Arg-Val-Gln

79) SEQ ID NO. 79:
AILLSQPPKQLGLRA
or

Ala-Ile-Leu-Leu-Ser-Gln-Pro-Pro-Lys-Gln-Leu-Gly-Leu-Arg-Ala

80) SEQ ID NO. 80:
PANTPLIFVFSLEAG
or

Pro-Ala-Asn-Thr-Pro-Leu-Ile-Phe-Val-Phe-Ser-Leu-Glu-Ala-Gly

81) SEQ ID NO. 81:
FHHICQAGLKLLTSG
or

Phe-His-His-Ile-Cys-Gln-Ala-Gly-Leu-Lys-Leu-Leu-Thr-Ser-Gly

82) SEQ ID NO. 82:
DPPASAFQSAGITGV
or

Asp-Pro-Pro-Ala-Ser-Ala-Phe-Gln-Ser-Ala-Gly-Ile-Thr-Gly-Val

83) SEQ ID NO. 83:
SHLTQPANLDKKICS
or

Ser-His-Leu-Thr-Gln-Pro-Ala-Asn-Leu-Asp-Lys-Lys-Ile-Cys-Ser

84) SEQ ID NO. 84:
NGGSCYVAQAGLKLLASCNPSK
or

Asn-Gly-Gly-Ser-Cys-Tyr-Val-Ala-Gln-Ala-Gly-Lys-Leu-Leu-Ala-Ser-Cys-Asn-Pro-Ser-Lys

85) SEQ ID NO. 85:
MWTLKSSLVLLLCLT
or

Met-Trp-Thr-Leu-Lys-Ser-Ser-Leu-Val-Leu-Leu-Leu-Cys-Leu-Thr

86) SEQ ID NO. 86:
CSYAFMFSSLRQKTS
or

Cys-Ser-Tyr-Ala-Phe-Met-Phe-Ser-Ser-Leu-Arg-Gln-Lys-Thr-Ser

87) SEQ ID NO. 87:
EPQGKVPCGEHFRIR
or

Glu-Pro-Gln-Gly-Lys-Val-Pro-Cys-Gly-Glu-His-Phe-Arg-Ile-Arg

-continued

88) SEQ ID NO. 88:
QNLPEHTQGWLGSKW
or

Gln-Asn-Leu-Pro-Glu-His-Thr-Gln-Gly-Trp-Leu-Gly-Ser-Lys-Trp

89) SEQ ID NO. 89:
LWLLFAVVPFVILKC
or

Leu-Trp-Leu-Leu-Phe-Ala-Val-Val-Pro-Phe-Val-Ile-Leu-Lys-Cys

90) SEQ ID NO. 90:
QRDSEKNKVRMAPFF
or

Gln-Arg-Asp-Ser-Glu-Lys-Asn-Lys-Val-Arg-Met-Ala-Pro-Phe-Phe

91) SEQ ID NO. 91:
LHHIDSISGVSGKRMF
or

Leu-His-His-Ile-Asp-Ser-Ile-Ser-Gly-Val-Ser-Gly-Lys-Arg-Met-Phe

92) SEQ ID NO. 92:
EAYYTMLHLPTTNRP
or

Glu-Ala-Tyr-Tyr-Thr-Met-Leu-His-Leu-Pro-Thr-Thr-Asn-Arg-Pro

93) SEQ ID NO. 93:
KIAHCILFNQPHSPR
or

Lys-Ile-Ala-His-Cys-Ile-Leu-Phe-Asn-Gln-Pro-His-Ser-Pro-Arg

94) SEQ ID NO. 94:
SNSHSHPNPLKLHRR
or

Ser-Asn-Ser-His-Ser-His-Pro-Asn-Pro-Leu-Lys-Leu-His-Arg-Arg

95) SEQ ID NO. 95:
SHSHNRPRAYILITI
or

Ser-His-Ser-His-Asn-Arg-Pro-Arg-Ala-Tyr-Ile-Leu-Ile-Thr-Ile

96) SEQ ID NO. 96:
LPSKLKLRTHSQSHH
or

Leu-Pro-Ser-Lys-Leu-Lys-Leu-Arg-Thr-His-Ser-Gln-Ser-His-His

97) SEQ ID NO. 97:
NPLSRTSNSTPTNSFLMTSSKPR
or

Asn-Pro-Leu-Ser-Arg-Thr-Ser-Asn-Ser-Thr-Pro-Thr-Asn-Ser-Phe-Leu-Met-Thr-Ser-Ser-Lys-Pro-Arg

98) SEQ ID NO. 98:
SSSLGLPKCWDYRHE
or

Ser-Ser-Ser-Leu-Gly-Leu-Pro-Lys-Cys-Trp-Asp-Tyr-Arg-His-Glu

99) SEQ ID NO. 99:
LLSLALMINFRVMAC
or

-continued
Leu-Leu-Ser-Leu-Ala-Leu-Met-Ile-Asn-Phe-Arg-Val-Met-Ala-Cys

100) SEQ ID NO. 100:
TFKQHIELRQKISIV
or

Thr-Phe-Lys-Gln-His-Ile-Glu-Leu-Arg-Gln-Lys-Ile-Ser-Ile-Val

101) SEQ ID NO. 101:
PRKLCCMGPVCPVKI
or

Pro-Arg-Lys-Leu-Cys-Cys-Met-Gly-Pro-Val-Cys-Pro-Val-Lys-Ile

102) SEQ ID NO. 102:
ALLTINGHCTWLPAS
or

Ala-Leu-Leu-Thr-Ile-Asn-Gly-His-Cys-Thr-Trp-Leu-Pro-Ala-Ser

103) SEQ ID NO. 103:
MFVFCLILNREKIKG
or

Met-Phe-Val-Phe-Cys-Leu-Ile-Leu-Asn-Arg-Glu-Lys-Ile-Lys-Gly

104) SEQ ID NO. 104:
GNSSFFLLSFFFSFQ
or

Gly-Asn-Ser-Ser-Phe-Phe-Leu-Leu-Ser-Phe-Phe-Ser-Phe-Gln

105) SEQ ID NO. 105:
NCCQCFQCRTTEGYA
or

Asn-Cys-Cys-Gln-Cys-Phe-Gln-Cys-Arg-Thr-Thr-Glu-Gly-Tyr-Ala

106) SEQ ID NO. 106:
VECFYCLVDKAAFECWWFYSFDT
or

Val-Glu-Cys-Phe-Tyr-Cys-Leu-Val-Asp-Lys-Ala-Ala-Phe-Glu-Cys-Trp-Trp-Phe-Tyr-Ser-Phe-Asp-Thr

107) SEQ ID NO. 107:
MEPHTVAQAGVPQHD
or

Met-Glu-Pro-His-Thr-Val-Ala-Gln-Ala-Gly-Val-Pro-Gln-His-Asp

108) SEQ ID NO. 108:
LGSLQSLLPRFKRFS
or

Leu-Gly-Ser-Leu-Gln-Ser-Leu-Leu-Pro-Arg-Phe-Lys-Arg-Phe-Ser

109) SEQ ID NO. 109:
CLILPKIWDYRNMNT
or

Cys-Leu-Ile-Leu-Pro-Lys-Ile-Trp-Asp-Tyr-Arg-Asn-Met-Asn-Thr

110) SEQ ID NO. 110:
ALIKRNRYTPETGRKS
or

Ala-Leu-Ile-Lys-Arg-Asn-Arg-Tyr-Thr-Pro-Glu-Thr-Gly-Arg-Lys-Ser

-continued
111) SEQ ID NO. 111:
IDQQVLSRI
or

Ile-Asp-Gln-Gln-Val-Leu-Ser-Arg-Ile

112) SEQ ID NO. 112:
KLEIKRCL
or

Lys-Leu-Glu-Ile-Lys-Arg-Cys-Leu

113) SEQ ID NO. 113:
VLSRIK
or

Val-Leu-Ser-Arg-Ile-Lys

114) SEQ ID NO. 114:
RIKLEIK
or

Arg-Ile-Lys-Leu-Glu-Ile-Lys

115) SEQ ID NO. 115:
VLSRIKLEIKRCL
or

Val-Leu-Ser-Arg-Ile-Lys-Leu-Glu-Ile-Lys-Arg-Cys-Leu,
and

116) SEQ ID NO. 116:
IDQQVLSRIKLEI
or

Ile-Asp-Gln-Gln-Val-Leu-Ser-Arg-Ile-Lys-Leu-Glu-Ile.

The expression "NTP peptide" also preferably includes (but is not limited to) the amino acid sequences of SEQ ID NO: 1 to 116.

The term "fragment" refers to a protein or polypeptide that consists of a continuous subsequence of the amino acid sequence of a protein or peptide and includes naturally occurring fragments such as splice variants and fragments resulting from naturally occurring in vivo protease activity. Such a fragment may be truncated at the amino terminus, the carboxy terminus, and/or internally (such as by natural splicing). Such fragments may be prepared with or without an amino terminal methionine. The term "fragment" includes fragments, whether identical or different, from the same protein or peptide, with a contiguous amino acid sequence in common or not, joined together, either directly or through a linker. A person having ordinary skill in the art will be capable of selecting a suitable fragment for use in the embodiments without undue experimentation using the guidelines and procedures outlined herein.

The term "variant" refers to a protein or polypeptide in which one or more amino acid substitutions, deletions, and/or insertions are present as compared to the amino acid sequence of an protein or peptide and includes naturally occurring allelic variants or alternative splice variants of an protein or peptide. The term "variant" includes the replacement of one or more amino acids in a peptide sequence with a similar or homologous amino acid(s) or a dissimilar amino acid(s). There are many scales on which amino acids can be ranked as similar or homologous. (Gunnar von Heijne, Sequence Analysis in Molecular Biology, p. 123-39 (Academic Press, New York, N.Y. 1987.) Preferred variants include alanine substitutions at one or more of amino acid positions. Other preferred substitutions include conservative substitutions that have little or no effect on the overall net charge, polarity, or hydrophobicity of the protein. Conservative substitutions are set forth in Table 2 below.

TABLE 2

Conservative Amino Acid Substitutions

| | |
|---|---|
| Basic: | arginine |
| | lysine |
| | histidine |
| Acidic: | glutamic acid |
| | aspartic acid |
| Uncharged Polar: | glutamine |
| | asparagine |
| | serine |
| | threonine |
| | tyrosine |
| Non-Polar: | phenylalanine |
| | tryptophan |
| | cysteine |
| | glycine |
| | alanine |
| | valine |
| | praline |
| | methionine |
| | leucine |
| | isoleucine |

Table 3 sets out another scheme of amino acid substitution:

TABLE 3

| Original Residue | Substitutions |
|---|---|
| Ala | gly;ser |
| Arg | lys |
| Asn | gln;his |
| Asp | glu |
| Cys | ser |
| Gln | asn |
| Glu | asp |
| Gly | ala;pro |
| His | asn;gln |
| Ile | eu;val |
| Leu | ile;val |
| Lys | arg;gln;glu |
| Met | leu;tyr;ile |
| Phe | met;leu;tyr |
| Ser | thr |
| Thr | ser |
| Trp | tyr |
| Tyr | trp;phe |
| Val | ile;leu |

Other variants can consist of less conservative amino acid substitutions, such as selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that in general are expected to have a more significant effect on function are those in which (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; or (e) a residue having a bulky side chain, e.g., phenylalanine, is substituted for (or by) one not having such a side chain, e.g., glycine. Other variants include those designed to either generate a novel glycosylation and/or phosphorylation site(s), or those designed to delete an existing glycosylation and/or phosphorylation site(s). Variants include at least one amino acid substitution at a glycosylation site, a proteolytic cleavage site and/or a cysteine residue. Variants also include proteins and peptides with additional amino acid residues before or after the protein or peptide amino acid sequence on linker peptides. For example, a cysteine residue may be added at both the amino and carboxy terminals of an NTP peptide in order to allow the cyclisation of the peptide by the formation of a di-sulphide bond. The term "variant" also encompasses polypeptides that have the amino acid sequence of an NTP peptide with at least one and up to 25 or more additional amino acids flanking either the 3' or 5' end of the peptide.

The term "derivative" refers to a chemically modified protein or polypeptide that has been chemically modified either by natural processes, such as processing and other post-translational modifications, but also by chemical modification techniques, as for example, by addition of one or more polyethylene glycol molecules, sugars, phosphates, and/or other such molecules, where the molecule or molecules are not naturally attached to wild-type proteins or NTP peptides. Derivatives include salts. Such chemical modifications are well described in basic texts and in more detailed monographs, as well as in a voluminous research literature, and they are well known to those of skill in the art. It will be appreciated that the same type of modification may be present in the same or varying degree at several sites in a given protein or polypeptide. Also, a given protein or polypeptide may contain many types of modifications. Modifications can occur anywhere in a protein or polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. See, for instance, Proteins—Structure And Molecular Properties, 2nd Ed., T. E. Creighton, W. H. Freeman and Company, New York (1993) and Wold, F., "Posttranslational Protein Modifications: Perspectives and Prospects," pgs. 1-12 in Post-translational Covalent Modification Of Proteins, B. C. Johnson, Ed., Academic Press, New York (1983); Seifter et al., Meth. Enzymol. 182:626-646 (1990) and Rattan et al., "Protein Synthesis: Posttranslational Modifications and Aging," Ann. N.Y. Acad. Sci. 663: 48-62 (1992). The term "derivatives" include chemical modifications resulting in the protein or polypeptide becoming branched or cyclic, with or without branching. Cyclic, branched and branched circular proteins or polypeptides may result from post-translational natural processes and may be made by entirely synthetic methods, as well.

The term "homologue" refers to a protein that is at least 60 percent identical in its amino acid sequence of an NTP peptide as determined by standard methods that are commonly used to compare the similarity in position of the amino acids of two polypeptides. The degree of similarity or identity between two proteins can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M Stockton Press, New York, 1991; and Carillo H. and Lipman, D., SIAM, J. Applied Math., 48:1073 (1988). Preferred methods to determine identity are designed to give the largest match between the sequences tested. Methods to determine identity and similarity are codified in publicly available computer programs.

Preferred computer program methods useful in determining the identity and similarity between two sequences include, but are not limited to, the GCG program package (Devereux, J., et al., Nucleic Acids Research, 12(1): 387 (1984)), BLASTP, BLASTN, and FASTA, Atschul, S. F. et al., J. Molec. Biol., 215: 403-410 (1990). The BLAST X program is publicly available from NCBI and other sources (BLAST Manual, Altschul, S., et al., NCBI NLM NIH Bethesda, Md. 20894; Altschul, S., et al., J. Mol. Biol., 215: 403-410 (1990). By way of example, using a computer algorithm such as GAP (Genetic Computer Group, University of Wisconsin, Madison, Wis.), the two proteins or polypeptides for which the percent sequence identity is to be determined are aligned for optimal matching of their respective amino acids (the "matched span", as determined by the algorithm).

A gap opening penalty (which is calculated as 3 times the average diagonal; the "average diagonal" is the average of the diagonal of the comparison matrix being used; the "diagonal" is the score or number assigned to each perfect amino acid match by the particular comparison matrix) and a gap extension penalty (which is usually {fraction (1/10)} times the gap opening penalty), as well as a comparison matrix such as PAM 250 or BLOSUM 62 are used in conjunction with the algorithm. A standard comparison matrix (see Dayhoff et al. in: Atlas of Protein Sequence and Structure, vol. 5, supp.3 for the PAM250 comparison matrix; see Henikoff et al., Proc. Natl. Acad. Sci USA, 89:10915-10919 for the BLOSUM 62 comparison matrix) also may be used by the algorithm. The percent identity then is calculated by the algorithm. Homologues will typically have one or more amino acid substitutions, deletions, and/or insertions as compared with the comparison protein or peptide, as the case may be.

The term "fusion protein" refers to a protein where one or more peptides are recombinantly fused or chemically conjugated (including covalently and non-covalently) to a protein such as (but not limited to) an antibody or antibody fragment like an $F_{ab}$ fragment or short chain Fv. The term "fusion protein" also refers to multimers (i.e. dimers, trimers, tetramers and higher multimers) of peptides. Such multimers comprise homomeric multimers comprising one peptide, heteromeric multimers comprising more than one peptide, and heteromeric multimers comprising at least one peptide and at least one other protein. Such multimers may be the result of hydrophobic, hyrdphilic, ionic and/or covalent associations, bonds or links, may be formed by cross-links using linker molecules or may be linked indirectly by, for example, liposome formation The term "peptide mimetic" or "mimetic" refers to biologically active compounds that mimic the biological activity of a peptide or a protein but are no longer peptidic in chemical nature, that is, they no longer contain any peptide bonds (that is, amide bonds between amino acids). Here, the term peptide mimetic is used in a broader sense to include molecules that are no longer completely peptidic in nature, such as pseudo-peptides, semi-peptides and peptoids. Examples of peptide mimetics in this broader sense (where part of a peptide is replaced by a structure lacking peptide bonds) are described below. Whether completely or partially non-peptide, peptide mimetics according to the embodiments provide a spatial arrangement of reactive chemical moieties that closely resemble the three-dimensional arrangement of active groups in the peptide on which the peptide mimetic is based. As a result of this similar active-site geometry, the peptide mimetic has effects on biological systems that are similar to the biological activity of the peptide.

The peptide mimetics of the embodiments are preferably substantially similar in both three-dimensional shape and biological activity to the peptides described herein. Examples of methods of structurally modifying a peptide known in the art to create a peptide mimetic include the inversion of backbone chiral centers leading to D-amino acid residue structures that may, particularly at the N-terminus, lead to enhanced stability for proteolytical degradation without adversely affecting activity. An example is given in the paper "Tritriated D-ala.sup.1-Peptide T Binding", Smith C. S. et al., Drug Development Res., 15, pp. 371-379 (1988). A second method is altering cyclic structure for stability, such as N to C interchain imides and lactames (Ede et al. in Smith and Rivier (Eds.) "Peptides: Chemistry and Biology", Escom, Leiden (1991), pp. 268-270). An example of this is given in conformationally restricted thymopentin-like compounds, such as those disclosed in U.S. Pat. No. 4,457,489 (1985), Goldstein, G. et al., the disclosure of which is incorporated by reference herein in its entirety. A third method is to substitute peptide bonds in the peptide by pseudopeptide bonds that. confer resistance to proteolysis.

A number of pseudopeptide bonds have been described that in general do not affect peptide structure and biological activity. One example of this approach is to substitute retro-inverso pseudopeptide bonds ("Biologically active retroinverso analogues of thymopentin", Sisto A. et al in Rivier, J. E. and Marshall, G. R. (eds) "Peptides, Chemistry, Structure and Biology", Escom, Leiden (1990), pp. 722-773) and Dalpozzo, et al. (1993), Int. J. Peptide Protein Res., 41:561-566, incorporated herein by reference). According to this modification, the amino acid sequences of the peptides may be identical to the sequences of an peptide described above, except that one or more of the peptide bonds are replaced by a retro-inverso pseudopeptide bond. Preferably the most N-terminal peptide bond is substituted, since such a substitution will confer resistance to proteolysis by exopeptidases acting on the N-terminus. Further modifications also can be made by replacing chemical groups of the amino acids with other chemical groups of similar structure. Another suitable pseudopeptide bond that is known to enhance stability to enzymatic cleavage with no or little loss of biological activity is the reduced isostere pseudopeptide bond (Couder, et al. (1993), Int. J. Peptide Protein Res., 41:181-184, incorporated herein by reference in its entirety).

Thus, the amino acid sequences of these peptides may be identical to the sequences of an peptide, except that one or more of the peptide bonds are replaced by an isostere pseudopeptide bond. Preferably the most N-terminal peptide bond is substituted, since such a substitution would confer resistance to proteolysis by exopeptidases acting on the N-terminus. The synthesis of peptides with one or more reduced isostere pseudopeptide bonds is known in the art (Couder, et al. (1993), cited above). Other examples include the introduction of ketomethylene or methylsulfide bonds to replace peptide bonds.

Peptoid derivatives of peptides represent another class of peptide mimetics that retain the important structural determinants for biological activity, yet eliminate the peptide bonds, thereby conferring resistance to proteolysis (Simon, et al., 1992, Proc. Natl. Acad. Sci. USA, 89:9367-9371, incorporated herein by reference in its entirety). Peptoids are oligomers of N-substituted glycines. A number of N-alkyl groups have been described, each corresponding to the side chain of a natural amino acid (Simon, et al. (1992), cited above). Some or all of the amino acids of the peptides may be replaced with the N-substituted glycine corresponding to the replaced amino acid.

The term "peptide mimetic" or "mimetic" also includes reverse-D peptides and enantiomers as defined below.

The term "reverse-D peptide" refers to a biologically active protein or peptide consisting of D-amino acids arranged in a reverse order as compared to the L-amino acid sequence of an peptide. Thus, the carboxy terminal residue of an L-amino acid peptide becomes the amino terminal for the D-amino acid peptide and so forth. For example, the peptide, ETESH (SEQ ID NO: 117 becomes $H_d S_d E_d T_d E_d$, where $E_d$, $H_d$, $S_d$, and $T_d$ are the D-amino acids corresponding to the L-amino acids, E, H, S, and T respectively.

The term "enantiomer" refers to a biologically active protein or peptide where one or more the L-amino acid residues in the amino acid sequence of an peptide is replaced with the corresponding D-amino acid residue(s).

A "composition" as used herein, refers broadly to any composition containing a recited peptide or amino acid sequence and, optionally an additional active agent. The composition may comprise a dry formulation, an aqueous solution, or a sterile composition. Compositions comprising peptides may be employed as hybridization probes. The probes may be stored in freeze-dried form and may be associated with a stabilizing agent such as a carbohydrate. In hybridizations, the probe may be deployed in an aqueous solution containing salts, e.g., NaCl, detergents, e.g., sodium dodecyl sulfate (SDS), and other components, e.g., Denhardt's solution, dry milk, salmon sperm DNA, etc.

The expression "clinically detected prostate cancer" denotes detecting prostate cancer clinically, and not through testing (e.g., PSA testing), or incidental detection. A person having ordinary skill in the art is familiar with the differences between clinical detection, incidental detection, and test-detection, and would know and understand that clinically detected prostate cancer typically involves performing a biopsy of the affected or surrounding tissue and determining whether that tissue includes cancerous cells. See, e.g., S. Srivastava et al., MOLECULAR PATHOLOGY OF EARLY CANCER, Chpt. 20 "Pathology and Molecular Biology of Early Prostate Cancer, Sakr and Grignon, pp. 301-320, IOS Press, 1999.

In an alternative embodiment in which an additional active agent is used together with the NTP Peptide, the expression "active agent" is used to denote any agent capable of removing unwanted cellular proliferations and/or tissue growth. Suitable active agents may include, but are not limited to: (i) anti-cancer active agents (such as alkylating agents, topoisomerase I inhibitors, topoisomerase II inhibitors, RNA/DNA antimetabolites, and antimitotic agents); (ii) active agents for treating benign growths such as anti-acne and anti-wart active agents; (iii) antiandrogen compounds, (cyproterone acetate (1α, 2β-methylene-6-chloro-17 α-acetoxy-6-dehydroprogesterone) Tamoxifen, aromatase inhibitors); (iv) alphal-adrenergic receptor blockers (tamsulosin, terazosin, doxazosin, prazosin, bunazosin, indoramin, alfulzosin, silodosin); (v) 5 α-reductase inhibitors (finasteride, dutasteride); (vi) phosphodiesterase type 5 (PDE5) inhibitors (tadalafil) and combinations thereof.

The embodiments are directed to methods of preventing or reducing the progression of prostate cancer, and to methods of reducing the incidence of prostate cancer in mammals comprising administering to a mammal in need thereof a therapeutically effective amount of a composition comprising an NTP peptide, either alone or in combination with at least one additional active agent capable of treating and/or killing unwanted cellular proliferations in mammals. In an embodiment, the mammals treated are those that had not previously been diagnosed with clinically detected prostate cancer. In other embodiment, the mammals treated are those that had been diagnosed with clinically detected prostate cancer. In another embodiment, the compositions are administered more than once.

Other peptide sequences derived from an NTP peptide found to be an effective agent for causing cell death also may be used as an additional active agent in combination with the NTP peptides described herein. A person ordinarily skilled in the art can, using the guidelines provided herein, synthesize without undue experimentation fragments of an effective Peptide spanning the entire amino acid sequence of that protein in order to identify other effective peptide sequences.

The inventor unexpectedly discovered that use of the NTP peptides in treating mammals in need of removal or destruction of unwanted cellular elements provided an unexpectedly superior reduction in the incidence of clinically detected prostate cancer, and provided an unexpectedly prevention or reduction in prostate cancer progression. The inventor unexpectedly discovered when conducting clinical trials for treating an unrelated disorder, BPH, that the administration of the NTP peptides, alone or in combination with another active agent, dramatically reduced the incidence of clinically detected prostate cancer when compared to the expected incidence in un-treated mammals. It has been reported that long term trial outcome results in mammals having BPH, have an incidence of clinically detected prostate cancer of greater than about 20%. Thompson, I M, et al., "The Influence of Finasteride on the Development of Prostate Cancer," *N Engl J Med*, Vol. 349, pp. 215-224 (2003); Andriole G L, et al., "Effect of Dutasteride on the Risk of Prostate Cancer," *N Engl J Med*, Vol. 362, pp. 1192-1202 (2010). The inventor discovered during clinical trials that the incidence of clinically detected prostate cancer in men suffering from BPH, when treated with a control (vehicle alone) was from about 5-6%.

In contrast to the published literature and the controls from the clinical trial, patients treated with the compositions of the present invention exhibited a dramatic decrease in the incidence of clinically detected prostate cancer. The method of the embodiments can prevent the incidence of clinically detected prostate cancer (incidence is 0%), or reduce the incidence rate, when compared to controls, by more than 15%, or by more than 20%, or by more than 25%, or by more than 30%, or by more than 40%, or by more than 50%, and by orders of magnitude, when compared to the known literature. The embodiments may result in an incidence of developing clinically detected prostate cancer within the range of from about 0% to about 5%, or from about 0% to about 4%, or from about 0% to about 3%, or from about 0% to about 2%, or from about 0% to about 1.5%, or from about 0% to about 1.3%, or from about 0% to about 1.0%, or from about 0% to about 0.8%.

The inventor also unexpectedly discovered when conducting clinical trials for treating an unrelated disorder, BPH, that the administration of the NTP peptides, alone or in combination with another active agent, dramatically reduced and/or prevented the progression of prostate cancer in patients at risk of developing prostate cancer. A patient at risk of developing prostate cancer is a patient having test-detected prostate cancer, such as having an elevated PSA level. In one embodiment, patients at risk of developing prostate cancer have a baseline PSA of more than 2.0, or more than 2.3, or more than 2.5. The inventor discovered that, for this subpopulation of patients, that administering the compositions of the embodiments resulted in a reduction in the incidence of clinically detected prostate cancer of from about 0% to less than about 5%, or from about 0% to less than about 4%, or from about 0% to less than about 3%, or from about 0% to less than about 2%, or from about 0% to less than about 1%, or from about 0% to about 0.5%, or from about 0% to about 0.2%, or about 0% (denoting prevention of progression of prostate cancer).

The embodiments include a method of treating a mammal suffering from a condition requiring the removal or destruction of unwanted cellular proliferations, comprising administering once or more than once an NTP peptide to the mammal, either alone or in combination with administration of an additional active agent. The method includes, but is not limited to, administering the NTP-peptides intramuscularly, orally, intravenously, intraperitoneally, intracerebrally (intraparenchymally), intracerebroyentricularly, intralesionally, intraocularly, intraarterially, intrathecally, intratumorally, intranasally, topically, transdermally, subcutaneously, or intradermally, either alone or conjugated to a carrier. The unwanted cellular proliferations include, inter alia, benign and malignant tumors, glandular (e.g. prostate) hyperplasia, and cancer. Preferred NTP peptides include one or more of the following:

```
                                           SEQ ID No. 66
IDQQVLSRIKLEIKRCL

Ile-Asp-Gln-Gln-Val-Leu-Ser-Arg-Ile-Lys-Leu-Glu-
Ile-Lys-Arg-Cys-Leu

SEQ ID NO. 111
IDQQVLSRI

Ile-Asp-Gln-Gln-Val-Leu-Ser-Arg-Ile

SEQ ID NO. 115
VLSRIKLEIKRCL

Val-Leu-Ser-Arg-Ile-Lys-Leu-Glu-Ile-Lys-Arg-Cys-
Leu

SEQ ID NO. 116
IDQQVLSRIKLEI

Ile-Asp-Gln-Gln-Val-Leu-Ser-Arg-Ile-Lys-Leu-Glu-
Ile
```

Any mammal can benefit from use of the invention, including humans, mice, rabbits, dogs, sheep and other livestock, any mammal treated or treatable by a veterinarian, zoo-keeper, or wildlife preserve employee. Preferred mammals are humans, sheep, and dogs. Throughout this description mammals and patients are used interchangeably.

It will be apparent to one of skill in the art that other smaller fragments of the above NTP peptides may be selected such that these peptides will possess the same or similar biological activity. Other fragments of may be selected by one skilled in the art such that these peptides will possess the same or similar biological activity. The peptides of the embodiments encompass these other fragments. In general, the peptides of the embodiments have at least 4 amino acids, preferably at least 5 amino acids, and more preferably at least 6 amino acids.

The embodiments also encompass methods of treating mammals (or patients) in need of removal or destruction of unwanted cellular proliferations comprising administering a composition comprising NTP peptides comprising two or more NTP peptides joined together, together with an additional active agent. To the extent that an NTP peptide has the desired biological activity, it follows that two such Peptides would also possess the desired biological activity.

NTP peptides and fragments, variants, derivatives, homologues, fusion proteins and mimetics thereof encompassed by this embodiment can be prepared using methods known to those of skill in the art, such as recombinant DNA technology, protein synthesis and isolation of naturally occurring peptides, proteins, AD7c-protein and fragments, variants, derivatives and homologues thereof.

NTP peptides and fragments, variants, derivatives, homologues, fusion proteins and mimetics thereof can be prepared from other peptides, proteins, and fragments, variants, derivatives and homologues thereof using methods known to those having skill in the art. Such methods include (but are not limited to) the use of proteases to cleave the peptide, or protein into the desired NTP peptides.

An NTP peptide can be prepared using well known recombinant DNA technology methods such as those set forth in Sambrook et al. Molecular Cloning: A Laboratory Manual, Cold Spring Harbor Laboratory Press, Cold Spring Harbor, N.Y. and/or Ausubel et al., eds., Current Protocols in Molecular Biology, Green Publishers Inc. and Wiley and Sons, N.Y.

A gene or cDNA encoding an NTP peptide may be obtained for example by screening a genomic or cDNA library, or by PCR amplification. Probes or primers useful for screening the library can be generated based on sequence information for other known genes or gene fragments from the same or a related family of genes, such as, for example, conserved motifs found in other peptides or proteins. In addition, where a gene encoding an NTP peptide has been identified, all or a portion of that gene may be used as a probe to identify homologous genes. The probes or primers may be used to screen cDNA libraries from various tissue sources believed to express an NTP peptide gene. Typically, conditions of high stringency will be employed for screening to minimize the number of false positives obtained from the screen.

Another means to prepare a gene encoding an NTP peptide is to employ chemical synthesis using methods well known to the skilled artisan, such as those described by Engels et al., Angew. Chem. Intl. Ed., 28:716-734. These methods include, inter alia, the phosphotriester, phosphoramidite, and H-phosphonate methods for nucleic acid synthesis. A preferred method for such chemical synthesis is polymer-supported synthesis using standard phosphoramidite chemistry. Typically, the DNA encoding an peptide or protein will be several hundred nucleotides in length. Nucleic acids larger than about 100 to nucleotides can be synthesized as several fragments using these methods. The fragments then can be ligated together to form the full length peptide or protein. Usually, the DNA fragment encoding the amino terminus of the protein will have an ATG, which encodes a methionine residue. This methionine may or may not be present on the mature form of the protein or peptide, depending on whether the protein produced in the host cell is designed to be secreted from that cell.

The gene, cDNA, or fragment thereof encoding the NTP peptide can be inserted into an appropriate expression or amplification vector using standard ligation techniques. The vector is typically selected to be functional in the particular host cell employed (i.e., the vector is compatible with the host cell machinery such that amplification of the gene and/or expression of the gene can occur). The gene, cDNA or fragment thereof encoding the NTP peptide may be amplified/expressed in prokaryotic, yeast, insect (baculovirus systems) and/or eukaryotic host cells. Selection of the host cell will depend in part on whether the NTP peptide is to be glycosylated and/or phosphorylated. If so, yeast, insect, or mammalian host cells are preferable.

Typically, the vectors used in any of the host cells will contain at least a 5' flanking sequence (also referred to as a promoter) and other regulatory elements as well, such as an enhancer(s), an origin of replication element, a transcriptional termination element, a complete intron sequence containing a donor and acceptor splice site, a signal peptide sequence, a ribosome binding site element, a polyadenylation sequence, a polylinker region for inserting the nucleic acid encoding the polypeptide to be expressed, and a selectable marker element. Each of these elements is discussed below. Optionally, the vector may contain a tag sequence, i.e., an oligonucleotide molecule located at the 5' or 3' end of the protein or peptide coding sequence; the oligonucleotide molecule encodes polyHis (such as hexaHis (SEQ ID NO: 118)), or other tag such as FLAG, HA (hemaglutinin Influenza virus) or myc for which commercially available antibodies exist. This tag is typically fused to the polypeptide upon expression of the polypeptide, and can serve as means for affinity purification of the protein or peptide from the host cell. Affinity purification can be accomplished, for example, by column chromatography using antibodies against the tag as an affinity matrix. Optionally, the tag can subsequently be removed from the purified protein or peptide by various means such as using certain peptidases.

The human immunoglobulin hinge and Fc region could be fused at either the N-terminus or C-terminus of the NTP peptide by one skilled in the art. The subsequent Fc-fusion protein could be purified by use of a Protein A affinity column. Fc is known to exhibit a long pharmacokinetic half-life in vivo and proteins fused to Fc have been found to exhibit a substantially greater half-life in vivo than the unfused counterpart. Also, fusion to the Fc region allows for dimerization/multimerization of the molecule that may be useful for the bioactivity of some molecules.

The 5' flanking sequence may be homologous (i.e., from the same species and/or strain as the host cell), heterologous (i.e., from a species other than the host cell species or strain), hybrid (i.e., a combination of 5' flanking sequences from more than one source), synthetic, or it may be the native protein or peptide gene 5' flanking sequence. As such, the source of the 5' flanking sequence may be any unicellular prokaryotic or eukaryotic organism, any vertebrate or invertebrate organism, or any plant, provided that the 5' flanking sequence is functional in, and can be activated by, the host cell machinery.

The 5' flanking sequences useful in the vectors of this embodiment may be obtained by any of several methods well known in the art. Typically, 5' flanking sequences useful herein other than the protein or peptide gene flanking sequence will have been previously identified by mapping and/or by restriction endonuclease digestion and can thus be isolated from the proper tissue source using the appropriate restriction endonucleases. In some cases, the full nucleotide sequence of the 5' flanking sequence may be known. Here, the 5' flanking sequence may be synthesized using the methods described above for nucleic acid synthesis or cloning. Where all or only a portion of the 5' flanking sequence is known, it may be obtained using PCR and/or by screening a genomic library with suitable oligonucleotide and/or 5' flanking sequence fragments from the same or another species.

Where the 5' flanking sequence is not known, a fragment of DNA containing a 5' flanking sequence may be isolated from a larger piece of DNA that may contain, for example, a coding sequence or even another gene or genes. Isolation may be accomplished by restriction endonuclease digestion using one or more carefully selected enzymes to isolate the proper DNA fragment. After digestion, the desired fragment may be isolated by agarose gel purification, Qiagen® column or other methods known to the skilled artisan. Selection of suitable enzymes to accomplish this purpose will be readily apparent to one of ordinary skill in the art.

The origin of replication element is typically a part of prokaryotic expression vectors purchased commercially, and aids in the amplification of the vector in a host cell. Amplification of the vector to a certain copy number can, in some cases, be important for optimal expression of the protein or peptide. If the vector of choice does not contain an origin of replication site, one may be chemically synthesized based on a known sequence, and ligated into the vector. The transcription termination element is typically located 3' of the end of the protein or peptide coding sequence and serves to terminate transcription of the protein or peptide. Usually, the transcription termination element in prokaryotic cells is a G-C rich fragment followed by a poly T sequence. While the element may be cloned from a library or purchased commercially as part of a vector, it can also be readily synthesized using methods for nucleic acid synthesis such as those described above.

A selectable marker gene element encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells, (b) complement auxotrophic deficiencies of the cell; or (c) supply critical nutrients not available from complex media. Preferred selectable markers are the kanamycin resistance gene, the ampicillin resistance gene, and the tetracycline resistance gene.

The ribosome binding element, commonly called the Shine-Dalgarno sequence (prokaryotes) or the Kozak sequence (eukaryotes), is usually necessary for translation initiation of mRNA. The element is typically located 3' to the promoter and 5' to the coding sequence of the protein or peptide to be synthesized. The Shine-Dalgarno sequence is varied but is typically a polypurine (i.e., having a high A-G content). Many Shine-Dalgarno sequences have been identified, each of which can be readily synthesized using methods set forth above and used in a prokaryotic vector.

In those cases where it is desirable for an NTP peptide to be secreted from the host cell, a signal sequence may be used to direct the Peptide out of the host cell where it is synthesized, and the carboxy-terminal part of the protein may be deleted in order to prevent membrane anchoring. Typically, the signal sequence is positioned in the coding region of the NTP peptide gene or cDNA, or directly at the 5' end of the Peptide gene coding region. Many signal sequences have been identified, and any of them that are functional in the selected host cell may be used in conjunction with the Peptide gene or cDNA. Therefore, the signal sequence may be homologous or heterologous to the Peptide gene or cDNA, and may be homologous or heterologous to the Peptide gene or cDNA. Additionally, the signal sequence may be chemically synthesized using methods set forth above. In most cases, secretion of the polypeptide from the host cell via the presence of a signal peptide will result in the removal of the amino terminal methionine from the polypeptide.

In many cases, transcription of the NTP peptide gene or cDNA is increased by the presence of one or more introns in the vector; this is particularly true where the Peptide is produced in eukaryotic host cells, especially mammalian host cells. The introns used may be naturally occurring within the Peptide gene, especially where the gene used is a full length genomic sequence or a fragment thereof. Where the intron is not naturally occurring within the gene (as for most cDNAs), the intron(s) may be obtained from another source. The position of the intron with respect to the flanking sequence and the Peptide gene generally is important, as the intron must be transcribed to be effective. As such, where the Peptide gene inserted into the expression vector is a cDNA molecule, the preferred position for the intron is 3' to the transcription start site, and 5' to the polyA transcription termination sequence. Preferably for Peptide cDNA, the intron or introns will be located on one side or the other (i.e., 5' or 3') of the cDNA such that it does not interrupt this coding sequence. Any intron from any source, including any viral, prokaryotic and eukaryotic (plant or animal) organisms, may be used to practice this embodiment, provided that it is compatible with the host cell(s) into which it is inserted. Also included herein are synthetic introns. Optionally, more than one intron may be used in the vector.

Where one or more of the elements set forth above are not already present in the vector to be used, they may be individually obtained and ligated into the vector. Methods used for obtaining each of the elements are well known to the skilled artisan and are comparable to the methods set forth above (i.e., synthesis of the DNA, library screening, and the like).

The final vectors used to practice this embodiment may be constructed from starting vectors such as a commercially available vector. Such vectors may or may not contain some of the elements to be included in the completed vector. If none of the desired elements are present in the starting vector, each element may be individually ligated into the vector by cutting the vector with the appropriate restriction endonuclease(s) such that the ends of the element to be ligated in and the ends of the vector are compatible for ligation. In some cases, it may be necessary to blunt the ends to be ligated together in order to obtain a satisfactory ligation. Blunting is accomplished by first filling in "sticky ends" using Klenow DNA polymerase or T4 DNA polymerase in the presence of all four nucleotides. This procedure is well known in the art and is described for example in Sambrook et al., supra. Alternatively, two or more of the elements to be inserted into the vector may first be ligated together (if they are to be positioned adjacent to each other) and then ligated into the vector.

An additional method for constructing the vector is to conduct all ligations of the various elements simultaneously in one reaction mixture. Here, many nonsense or nonfunctional vectors will be generated due to improper ligation or insertion of the elements, however the functional vector may be identified and selected by restriction endonuclease digestion.

Preferred vectors for practicing this embodiment are those that are compatible with bacterial, insect, and mammalian host cells. Such vectors include, inter alia, pCRII, pCR3, and pcDNA3.1 (Invitrogen Company, San Diego, Calif.), pBSII (Stratagene Company, La Jolla, Calif.), pET15b (Novagen, Madison, Wis.), PGEX (Pharmacia Biotech, Piscataway, N.J.), pEGFP-N2 (Clontech, Palo Alto, Calif.), pETL (BlueBachl; Invitrogen), and pFastBacDual (Gibco/BRL, Grand Island, N.Y.).

After the vector has been constructed and a nucleic acid molecule encoding full length or truncated protein or peptide has been inserted into the proper site of the vector, the completed vector may be inserted into a suitable host cell for amplification and/or polypeptide expression. Host cells may be prokaryotic host cells (such as $E.\ coli$) or eukaryotic host cells (such as a yeast cell, an insect cell, or a vertebrate cell). The host cell, when cultured under appropriate conditions, can synthesize protein or peptide which can subsequently be collected from the culture medium (if the host cell secretes it into the medium) or directly from the host cell producing it (if it is not secreted).

After collection, the NTP peptide can be purified using methods such as molecular sieve chromatography, affinity chromatography, and the like. Selection of the host cell for protein or peptide production will depend in part on whether the Peptide is to be glycosylated or phosphorylated (in which case eukaryotic host cells are preferred), and the manner in which the host cell is able to fold the Peptide into its native tertiary structure (e.g., proper orientation of disulfide bridges, etc.) such that biologically active protein is prepared by the Peptide that has biological activity, the Peptide may be folded after synthesis using appropriate chemical conditions as discussed below. Suitable cells or cell lines may be mammalian cells, such as Chinese hamster ovary cells (CHO), human embryonic kidney (HEK) 293, 293T cells, or 3T3 cells. The selection of suitable mammalian host cells and methods for transformation, culture, amplification, screening and product production and purification are known in the art. Other suitable mammalian cell lines, are the monkey COS-1 and COS-7 cell lines, and the CV-1 cell line. Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Other suitable mammalian cell lines include but are not limited to, mouse neuroblastoma N2A cells, HeLa, mouse L-929 cells, 3T3 lines derived from Swiss, Balb-c or NIH mice, BHK or HaK hamster cell lines.

Similarly useful as host cells suitable for the present embodiments are bacterial cells. For example, the various strains of $E.\ coli$ (e.g., HB101, DH5.alpha., DH10, and MC1061) are well-known as host cells in the field of biotechnology. Various strains of $B.\ subtilis$, Pseudomonas spp., other Bacillus spp., Streptomyces spp., and the like may also be employed in this method. Many strains of yeast cells known to those skilled in the art also are available as host cells for expression of the polypeptides of the present embodiments.

Additionally, where desired, insect cell systems may be utilized in the methods of the present embodiments. Such systems are described for example in Kitts et al. (Biotechniques, 14:810-817), Lucklow (Curr. Opin. Biotechnol., 4:564-572) and Lucklow et al. (J. Virol., 67:4566-4579). Preferred insect cells are Sf-9 and Hi5 (Invitrogen, Carlsbad, Calif.).

Insertion (also referred to as transformation or transfection) of the vector into the selected host cell may be accomplished using such methods as calcium chloride, electroporation, microinjection, lipofection, or the DEAE-dextran method. The method selected will in part be a function of the type of host cell to be used. These methods and other suitable methods are well known to the skilled artisan, and are set forth, for example, in Sambrook et al., supra.

The host cells containing the vector (i.e., transformed or transfected) may be cultured using standard media well known to the skilled artisan. The media will usually contain all nutrients necessary for the growth and survival of the cells. Suitable media for culturing E. coli cells are for example, Luria Broth (LB) and/or Terrific Broth (TB). Suitable media for culturing eukaryotic cells are RPMI 1640, MEM, DMEM, all of which may be supplemented with serum and/or growth factors as required by the particular cell line being cultured. A suitable medium for insect cultures is Grace's medium supplemented with yeastolate, lactalbumin hydrolysate, and/or fetal calf serum as necessary. Typically, an antibiotic or other compound useful for selective growth of the transformed cells only is added as a supplement to the media. The compound to be used will be dictated by the selectable marker element present on the plasmid with which the host cell was transformed. For example, where the selectable marker element is kanamycin resistance, the compound added to the culture medium will be kanamycin.

The amount of NTP peptide produced in the host cell can be evaluated using standard methods known in the art. Such methods include, without limitation, Western blot analysis, SDS-polyacrylamide gel electrophoresis, non-denaturing gel electrophoresis, HPLC separation, mass spectroscopy, immunoprecipitation, and/or activity assays such as DNA binding gel shift assays.

If the protein or peptide has been designed to be secreted from the host cells, the majority of the protein or peptide may be found in the cell culture medium. Proteins prepared in this way will typically not possess an amino terminal methionine, as it is removed during secretion from the cell. If however, the protein or peptide is not secreted from the host cells, it will be present in the cytoplasm and/or the nucleus (for eukaryotic host cells) or in the cytosol (for gram negative bacteria host cells) and may have an amino terminal methionine.

For an NTP peptide situated in the host cell cytoplasm and/or nucleus, the host cells are typically first disrupted mechanically or with detergent to release the intra-cellular contents into a buffered solution. The Peptide can then be isolated from this solution.

Purification of NTP peptides from solution can be accomplished using a variety of techniques. If the NTP peptide has been synthesized such that it contains a tag such as hexa-Histidine (SEQ ID NO: 118) (e.g. peptide/hexaHis (SEQ ID NO: 118)) or other small peptide such as FLAG (Sigma-Aldritch, St. Louis, Mo.) or calmodulin-binding peptide (Stratagene, La Jolla, Calif.) at either its carboxyl or amino terminus, it may essentially be purified in a one-step process by passing the solution through an affinity column where the column matrix has a high affinity for the tag or for the protein directly (i.e., a monoclonal antibody specifically recognizing the peptide). For example, polyhistidine binds with great affinity and specificity to nickel, zinc and cobalt; thus immobilized metal ion affinity chromatography which employs a nickel-based affinity resin (as used in Qiagen's QIAexpress system or Invitrogen's Xpress System) or a cobalt-based affinity resin (as used in BD Biosciences-CLONTECH's Talon system) can be used for purification of peptide/polyHis. (See, for example, Ausubel et al., eds., Current Protocols in Molecular Biology, Section 10.11.8, John Wiley & Sons, New York).

Where the NTP peptide is prepared without a tag attached, and no antibodies are available, other well known procedures for purification can be used. Such procedures include, without limitation, ion exchange chromatography, hydroxyapatite chromatography, hydrophobic interaction chromatography, molecular sieve chromatography, HPLC, native gel electrophoresis in combination with gel elution, and preparative isoelectric focusing (Isoprime machine/technique, Hoefer Scientific). In some cases, two or more of these techniques may be combined to achieve increased purity.

If it is anticipated that the NTP peptide will be found primarily intracellularly, the intracellular material (including inclusion bodies for gram-negative bacteria) can be extracted from the host cell using any standard technique known to the skilled artisan. For example, the host cells can be lysed to release the contents of the periplasm/cytoplasm by French press, homogenization, and/or sonication followed by centrifugation. If the Peptide has formed inclusion bodies in the cytosol, the inclusion bodies can often bind to the inner and/or outer cellular membranes and thus will be found primarily in the pellet material after centrifugation. The pellet material then can be treated at pH extremes or with chaotropic agent such as a detergent, guanidine, guanidine derivatives, urea, or urea derivatives in the presence of a reducing agent such as dithiothreitol at alkaline pH or tris carboxyethyl phosphine at acid pH to release, break apart, and solubilize the inclusion bodies. The Peptide in its now soluble form can then be analyzed using gel electrophoresis, immunoprecipitation or the like. If it is desired to isolate the Peptide, isolation may be accomplished using standard methods such as those set forth below and in Marston et al. Meth. Enz., 182:264-275.

In some cases, the NTP peptide may not be biologically active upon isolation. Various methods for refolding or converting the polypeptide to its tertiary structure and generating disulfide linkages, can be used to restore biological activity. Such methods include exposing the solubilized polypeptide to a pH usually above 7 and in the presence of a particular concentration of a chaotrope. The selection of chaotrope is very similar to the choices used for inclusion body solubilization but usually at a lower concentration and is not necessarily the same chaotrope as used for the solubilization. In most cases the refolding/oxidation solution will also contain a reducing agent or the reducing agent plus its, oxidized form in a specific ratio to generate a particular redox potential allowing for disulfide shuffling to occur in the formation of the protein's cysteine bridge(s). Some of the commonly used redox couples include cysteine/cystamine, glutathione (GSH)/dithiobis GSH, cupric chloride, dithiothreitol(DTT)/dithiane DTT, 2-mercaptoethanol (bME)/dithio-b(ME). In many instances a cosolvent is necessary to increase the efficiency of the refolding and the more common reagents used for this purpose include glycerol, polyethylene glycol of various molecular weights, and arginine.

If NTP peptide inclusion bodies are not formed to a significant degree in the host cell, the NTP peptide will be found primarily in the supernatant after centrifugation of the cell homogenate, and the NTP peptide can be isolated from the supernatant using methods such as those set forth below.

In those situations where it is preferable to partially or completely isolate the NTP peptide, purification can be accomplished using standard methods well known to the skilled artisan. Such methods include, without limitation, separation by electrophoresis followed by electroelution, various types of chromatography (immunoaffinity, molecular sieve, and/or ion exchange), and/or high pressure liquid chromatography. In some cases, it may be preferable to use more than one of these methods for complete purification.

In addition to preparing and purifying NTP peptides using recombinant DNA techniques, the NTP peptides and their fragments, variants, homologues, fusion proteins, peptide mimetics, and derivatives may be prepared by chemical synthesis methods (such as solid phase peptide synthesis) using techniques known in the art such as those set forth by Merrifield et al., J. Am. Chem. Soc., 85:2149, Houghten et al. Proc Natl Acad. Sci. USA, 82:5132, and Stewart and Young, Solid Phase Peptide Synthesis, Pierce Chemical Co., Rockford, Ill. Such Peptides may be synthesized with or without a methionine on the amino terminus. Chemically synthesized NTP peptides may be oxidized using methods set forth in these references to form disulfide bridges. The NTP peptides are expected to have biological activity comparable to Peptides produced recombinantly or purified from natural sources, and thus may be used interchangeably with recombinant or natural Peptide.

Chemically modified NTP peptide compositions in which the Peptide is linked to a polymer are included within the scope of the present embodiments. The polymer selected is typically water soluble so that the protein to which it is attached does not precipitate in an aqueous environment, such as a physiological environment. The polymer selected is usually modified to have a single reactive group, such as an active ester for acylation or an aldehyde for alkylation, so that the degree of polymerization may be controlled as provided for in the present methods. The polymer may be of any molecular weight, and may be branched or unbranched. Included within the scope of peptide polymers is a mixture of polymers.

In some cases, it may be desirable to prepare nucleic acid and/or amino acid variants of the naturally occurring NTP peptides. Nucleic acid variants may be produced using site directed mutagenesis, PCR amplification, or other appropriate methods, where the primer(s) have the desired point mutations (see Sambrook et al., supra, and Ausubel et al., supra, for descriptions of mutagenesis techniques). Chemical synthesis using methods described by Engels et al., supra, may also be used to prepare such variants. Other methods known to the skilled artisan may be used as well.

Preferred nucleic acid variants are those containing nucleotide substitutions accounting for codon preference in the host cell that is to be used to produce NTP peptides. Such codon optimization can be determined via computer algorithers which incorporate codon frequency tables such as Ecohigh. Cod for codon preference of highly expressed bacterial genes as provided by the University of Wisconsin Package Version 9.0, Genetics Computer Group, Madison, Wis. Other useful codon frequency tables include Celegans_high.cod, Celegans_low.cod, Drosophila_high.cod, Human_high.cod, Maize_high.cod, and Yeast_high.cod. Other preferred variants are those encoding conservative amino acid changes as described above (e.g., wherein the charge or polarity of the naturally occurring amino acid side chain is not altered substantially by substitution with a different amino acid) as compared to wild type, and/or those designed to either generate a novel glycosylation and/or phosphorylation site(s), or those designed to delete an existing glycosylation and/or phosphorylation site(s).

NTP peptides and fragments, homologs, variants, fusion proteins, peptide mimetics, derivatives and salts thereof also can be made using conventional peptide synthesis techniques known to the skilled artisan. These techniques include chemical coupling methods (cf. Wunsch, E: "Methoden der organischen Chemie", Volume 15, Band 1+2, Synthese von Peptiden, thime Verlag, Stuttgart (1974), and Barrany, G.; Merrifield, R. B.: "The Peptides," eds. E. Gross, J. Meienhofer, Volume 2, Chapter 1, pp. 1-284, Academic Press (1980)), enzymatic coupling methods (cf. Widmer, F. Johansen, J. T., Carlsberg Res. Commun., Vol. 44, pp. 37-46 (1979); Kullmann, W.: "Enzymatic Peptide Synthesis", CRC Press Inc. Boca Raton, Fla. (1987); and Widmer, F., Johansen, J. T. in "Synthetic Peptides in Biology and Medicines," eds. Alitalo, K., Partanen, P., Vatieri, A., pp. 79-86, Elsevier, Amsterdam (1985)), or a combination of chemical and enzymatic methods if this is advantageous for the process design and economy. Using the guidelines provided herein, those skilled in the art are capable of varying the peptide sequence of the NTP peptide to make a homologue having the same or similar biological activity (bioactivity) as the original or native NTP peptide.

Advantages exist for using a mimetic of a given NTP peptide rather than the Peptide itself. In general, peptide mimetics are more bioavailable, have a longer duration of action and can be cheaper to produce than the native proteins and peptides.

Peptide mimetics of NTP peptides can be developed using combinatorial chemistry techniques and other techniques known in the art (see e.g. Proceedings of the 20th European Peptide Symposium, ed. G. Jung, E. Bayer, pp. 289-336, and references therein). Examples of methods known in the art for structurally modifying a peptide to create a peptide mimetic include the inversion of backbone chiral centers leading to D-amino acid residue structures that may, particularly at the N-terminus, lead to enhanced stability for proteolytical degradation without adversely affecting activity. An example is provided in the paper "Tritriated D-ala$^1$-Peptide T Binding", Smith C. S. et al., Drug Development Res. 15, pp. 371-379 (1988).

A second method is altering cyclic structure for stability, such as N to C interchain imides and lactames (Ede et al. in Smith and Rivier (Eds.) "Peptides: Chemistry and Biology", Escom, Leiden (1991), pp. 268-270). An example of this is given in conformationally restricted thymopentin-like compounds, such as those disclosed in U.S. Pat. No. 4,457,489 (1985), Goldstein, G. et al., the disclosure of which is incorporated by reference herein in its entirety.

A third method is to substitute peptide bonds in the NTP peptide by pseudopeptide bonds that confer resistance to proteolysis. A number of pseudopeptide bonds have been described that in general do not affect peptide structure and biological activity. One example of this approach is to substitute retro-inverso pseudopeptide bonds ("Biologically active retroinverso analogues of thymopentin", Sisto A. et al in Rivier, J. E. and Marshall, G. R. (eds) "Peptides, Chemistry, Structure and Biology", Escom, Leiden (1990), pp. 722-773) and Dalpozzo, et al. (1993), Int. J. Peptide Protein Res., 41:561-566, incorporated herein by reference). According to this modification, the amino acid sequences of the peptides may be identical to the sequences of the peptides described above, except that one or more of the peptide bonds are replaced by a retro-inverso pseudopeptide bond. Preferably the most N-terminal peptide bond is substituted, since such a substitution will confer resistance to proteolysis by exopeptidases acting on the N-terminus.

The synthesis of peptides with one or more reduced retro-inverso pseudopeptide bonds is known in the art (Sisto (1990) and Dalpozzo, et al. (1993), cited above). Thus, peptide bonds can be replaced by non-peptide bonds that allow the peptide mimetic to adopt a similar structure, and therefore biological activity, to the original peptide. Further modifications also can be made by replacing chemical groups of the amino acids with other chemical groups of similar structure. Another suitable pseudopeptide bond that is known to enhance stability to enzymatic cleavage with no or little loss of biological activity is the reduced isostere pseudopeptide bond is a (Couder, et al. (1993), Int. J. Peptide Protein Res., 41:181-184, incorporated herein by reference in its entirety). Thus, the amino acid sequences of these peptides may be identical to the sequences of an peptide, except that one or more of the peptide bonds are replaced by an isostere pseudopeptide bond. Preferably the most N-terminal peptide bond is substituted, since such a substitution would confer resistance to proteolysis by exopeptidases acting on the N-terminus. The synthesis of peptides with one or more reduced isostere pseudopeptide bonds is known in the art (Couder, et al. (1993), cited above). Other examples include the introduction of ketomethylene or methylsulfide bonds to replace peptide bonds.

Peptoid derivatives of NTP peptides represent another class of peptide mimetics that retain the important structural determinants for biological activity, yet eliminate the peptide bonds, thereby conferring resistance to proteolysis (Simon, et al., 1992, Proc. Natl. Acad. Sci. USA, 89:9367-9371 and incorporated herein by reference in its entirety). Peptoids are oligomers of N-substituted glycines. A number of N-alkyl groups have been described, each corresponding to the side chain of a natural amino acid (Simon, et al. (1992), cited above and incorporated herein by reference in its entirety). Some or all of the amino acids of the peptide are replaced with the N-substituted glycine corresponding to the replaced amino acid.

The development of peptide mimetics can be aided by determining the tertiary structure of the original peptide by NMR spectroscopy, crystallography and/or computer-aided molecular modeling. These techniques aid in the development of novel compositions of higher potency and/or greater bioavailability and/or greater stability than the original peptide (Dean (1994), BioEssays, 16: 683-687; Cohen and Shatzmiller (1993), J. Mol. Graph., 11: 166-173; Wiley and Rich (1993), Med. Res. Rev., 13: 327-384; Moore (1994), Trends Pharmacol. Sci., 15: 124-129; Hruby (1993), Biopolymers, 33: 1073-1082; Bugg et al. (1993), Sci. Am., 269: 92-98, all incorporated herein by reference in their entirety).

Once a potential peptide mimetic compound is identified, it may be synthesized and assayed using the methods outlined in the examples below to assess its activity. The peptide mimetic compounds obtained by the above methods, having the biological activity of the peptides and similar three-dimensional structure, are encompassed by this embodiment. It will be readily apparent to one skilled in the art that a peptide mimetic can be generated from any of the peptides bearing one or more of the modifications described above. It will furthermore be apparent that the peptide mimetics of this embodiment can be further used for the development of even more potent non-peptidic compounds, in addition to their utility as therapeutic compounds.

A number of organizations exist today that are capable of synthesizing the peptides described herein. For example, given the sequence of an NTP peptide, the organization can synthesize the Peptide and forward the synthesized Peptide with accompanying documentation and proof of the identity of the Peptide.

The present embodiments are directed to methods of treating mammals with conditions requiring removal of cells, such as benign and malignant tumors, glandular (e.g. prostate) hyperplasia, cancer in which the treatment reduces the incidence of clinically developed prostate cancer, or prevents or reduces the progression of prostate cancer in patients at risk of developing prostate cancer. Such a method comprises administering to a mammal in need thereof, a therapeutically effective amount of NTP peptide, either alone, or in combination with an additional active agent. The mammals in need may be mammals suffering from benign prostatic hyperplasia, that may or may not be at increased risk of developing prostate cancer, or mammals at risk of developing prostate cancer. The mammals in need also may be any mammal that would benefit from a reduction in the incidence of clinically detected prostate cancer.

The additional active agent, if used, can be one or more active agents selected from (i) anti-cancer active agents (such as alkylating agents, topoisomerase I inhibitors, topoisomerase II inhibitors, RNA/DNA antimetabolites, and antimitotic agents); (ii) active agents for treating benign growths such as anti-acne and anti-wart active agents (salicylic acid); (iii) antiandrogen compounds, (cyproterone acetate (1α, 2β-methylene-6-chloro-17 α-acetoxy-6-dehydroprogesterone)) Tamoxifen, aromatase inhibitors); (iv) alpha1-adrenergic receptor blockers (tamsulosin, terazosin, doxazosin, prazosin, bunazosin, indoramin, alfulzosin, silodosin); (v) 5 α-reductase inhibitors (finasteride, dutasteride); (vi) phosphodiesterase type 5 (PDE5) inhibitors (tadalafil) and combinations thereof. Preferably, the additional active agent is selected from the group consisting of tamsulosin, finasteride, terazosin, doxazosin, prazosin, tadalafil, alfuzosin, silodosin, dutasteride, combinations of dutasteride and tamsulosin, and mixtures and combinations thereof.

The condition can be, for example, tumors of lung, breast, stomach, pancreas, prostate, bladder, bone, ovary, skin, kidney, sinus, colon, intestine, stomach, rectum, esophagus, blood, brain and its coverings, spinal cord and its coverings, muscle, connective tissue, adrenal, parathyroid, thyroid, uterus, testis, pituitary, reproductive organs, liver, gall bladder, eye, ear, nose, throat, tonsils, mouth, lymph nodes and lymphoid system, and other organs. In certain embodiments, the condition is benign prostatic hyperplasia, and in other embodiments, the condition is prostate cancer.

As used herein, the term "malignant tumor" is intended to encompass all forms of human carcinomas, sarcomas and melanomas which occur in the poorly differentiated, moderately differentiated, and well-differentiated forms.

The condition to be treated can also be a hyperplasia, hypertrophy, or overgrowth of a tissue selected from the group consisting of lung, breast, stomach, pancreas, prostate, bladder, bone, ovary, skin, kidney, sinus, colon, intestine, stomach, rectum, esophagus, blood, brain and its coverings, spinal cord and its coverings, muscle, connective tissue, adrenal, parathyroid, thyroid, uterus, testis, pituitary, reproductive organs, liver, gall bladder, eye, ear, nose, throat, tonsils, mouth, and lymph nodes and lymphoid system.

Other conditions that can be treated using the method of the embodiments are virally, bacterially, or parasitically altered tissue selected from the group consisting of lung, breast, stomach, pancreas, prostate, bladder, bone, ovary, skin, kidney, sinus, colon, intestine, stomach, rectum, esophagus, blood, brain and its coverings, spinal cord and its coverings, muscle, connective tissue, adrenal, parathyroid, thyroid, uterus, testis, pituitary, reproductive organs, liver, gall bladder, eye, ear, nose, throat, tonsils, mouth, and lymph nodes and lymphoid system.

The condition to be treated can also be a malformation or disorder of a tissue selected from the group consisting of lung, breast, stomach, pancreas, prostate, bladder, bone, ovary, skin, kidney, sinus, colon, intestine, stomach, rectum, esophagus, blood, brain and its coverings, spinal cord and its coverings, muscle, connective tissue, adrenal, parathyroid, thyroid, uterus, testis, pituitary, reproductive organs, liver, gall bladder, eye, ear, nose, throat, tonsils, mouth, and lymph nodes and lymphoid system.

In particular, the condition to be treated can be tonsillar hypertrophy, prostatic hyperplasia, psoriasis, eczema, dermatoses or hemorrhoids. The condition to be treated can be a vascular disease, such as atherosclerosis or arteriosclerosis, or a vascular disorder, such as varicose veins, stenosis or restenosis of an artery or a stent. The condition to be treated can also be a cosmetic modification to a tissue, such as skin, eye, ear, nose, throat, mouth, muscle, connective tissue, hair, or breast tissue.

Therapeutic compositions of NTP peptides may comprise a therapeutically effective amount of an NTP peptide in admixture with a pharmaceutically acceptable carrier. In some alternative embodiments, the additional active agent can be administered in the same composition with the NTP peptide, and in other embodiments, the composition comprising the NTP peptide is administered as an injection, whereas the additional active agent is formulated into an oral medication (gel, capsule, tablet, liquid, etc.). The carrier material may be water for injection, preferably supplemented with other materials common in solutions for administration to mammals. Typically, an NTP peptide for therapeutic use will be administered in the form of a composition comprising purified peptide in conjunction with one or more physiologically acceptable carriers, excipients, or diluents. Neutral buffered saline or saline mixed with serum albumin are exemplary appropriate carriers. Preferably, the product is formulated as a lyophilizate using appropriate excipients (e.g., sucrose). Other standard carriers, diluents, and excipients may be included as desired. Compositions of the embodiments also may comprise buffers known to those having ordinary skill in the art with an appropriate range of pH values, including Tris buffer of about pH 7.0-8.5, or acetate buffer of about pH 4.0-5.5, which may further include sorbitol or a suitable substitute therefor.

The use of NTP peptides conjugated or linked or bound to an antibody, antibody fragment, antibody-like molecule, or a molecule with a high affinity to a specific tumor marker, such as a cellular receptor, signal peptide or over-expressed enzyme, for targeting to the unwanted cellular elements in a naïve mammal also is encompassed by the scope of the embodiments. The antibody, antibody fragment, antibody-like molecule, or molecule with a high affinity to a specific tumor marker is used to target the Peptide conjugate to a specific cellular or tissue target. For example, a tumor with a distinctive surface antigen or expressed antigen can be targeted by the antibody, antibody fragment, or antibody-like binding molecule and the tumor cells can be killed by the Peptide. Such an approach using antibody targeting has the anticipated advantages of decreasing dosage, increasing the likelihood of binding to and uptake by the target cells, and increased usefulness for targeting and treating metastatic tumors and microscopic sized tumors.

The embodiments also encompass the use of NTP peptides conjugated or linked or bound to a protein or other molecule to form a composition that, upon cleavage at or near the site(s) of the tumor or other unwanted cells by a tumor- or site-specific enzyme or protease or by an antibody conjugate that targets tumor or other unwanted cells, releases the Peptide at or near the site(s) of the tumor or other unwanted cells The embodiments also encompass the use of NTP peptides conjugated or linked or bound to a protein or other molecule to form a composition that releases the Peptide or some biologically active fragment of the Peptide upon exposure of the tissue to be treated to light (as in laser therapies or other photo-dynamic or photo-activated therapy), other forms of electromagnetic radiation such as infra-red radiation, ultraviolet radiation, x-ray or gamma ray radiation, localized heat, alpha or beta radiation, ultrasonic emissions, or other sources of localized energy.

The embodiments also encompass therapeutic compositions of NTP peptides employing dendrimers, fullerenes, and other synthetic molecules, polymers and macromolecules where the Peptide and/or its corresponding DNA molecule is conjugated with, attached to or enclosed in the molecule, polymer or macromolecule, either by itself or in conjunction with other species of molecule such as a tumor-specific marker. For example, U.S. Pat. No. 5,714,166, Bioactive and/or Targeted Dendimer Conjugates, provides a method of preparing and using, inter alia, dendritic polymer conjugates composed of at least one dendrimer with a target director(s) and at least one bioactive agent conjugated to it. The disclosure of U.S. Pat. No. 5,714,166 is incorporated by reference herein in its entirety.

The embodiments also encompasses methods of treating mammals with therapeutic compositions of NTP peptides and/or genes and drug delivery vehicles such as lipid emulsions, micelle polymers, polymer microspheres, electroactive polymers, hydrogels and liposomes, in combination with an additional active agent.

The use of NTP peptides or related genes or gene equivalents transferred to the unwanted cells in a mammal also is encompassed by the embodiments. Overexpression of the NTP peptide within the tumor can be used to induce the cells in the tumor to die and thus reduce the tumor cell population. The gene or gene equivalent transfer of NTP peptide to treat the unwanted cellular elements is anticipated to have the advantage of requiring less dosage, and of being passed on to the cellular progeny of the targeted cellular elements, thus necessitating less frequent therapy, and less total therapy. This embodiment also encompasses the transfer of genes that code for a fusion protein containing an NTP peptide to the unwanted cells or neighboring cells where, following the expression of the gene and the production and/or secretion of the fusion protein, the fusion protein is cleaved either by native enzymes or proteases or by a prodrug to release the NTP peptide in, at or near the unwanted cells.

The use of cloned recombinant peptide-antibody conjugates; cloned recombinant peptide-antibody fragment conjugates; and cloned recombinant peptide-antibody-like protein conjugates for administration to treatment naïve mammals also is encompassed by the scope of the embodiments. The advantages of a cloned NTP peptide combined with targeting conjugate (such as an antibody, antibody fragment, antibody-like molecule, or a molecule with a high affinity to a cancer-specific receptor or other tumor marker) are that such a molecule combines the targeting advantages described above in addition to advantages for manufacturing and standardized production of the cloned conjugated molecule.

The embodiments further include the use of therapeutic compositions of NTP peptides or genes or gene equivalents as a component of the coating of a medical device such as a stent in order to remove, inhibit or prevent unwanted cellular proliferation or accumulation, in combination with an additional active agent.

Solid dosage forms for oral administration include but are not limited to, capsules, tablets, pills, powders, and granules. In such solid dosage forms, the additional active agent, and/or the NTP peptide can be admixed with at least one of the following: (a) one or more inert excipients (or carrier), such as sodium citrate or dicalcium phosphate; (b) fillers or extenders, such as starches, lactose, sucrose, glucose, mannitol, and silicic acid; (c) binders, such as carboxymethylcellulose, alginates, gelatin, polyvinylpyrrolidone, sucrose and acacia; (d) humectants, such as glycerol; (e) disintegrating agents, such as agar-agar, calcium carbonate, potato or tapioca starch, alginic acid, certain complex silicates, and sodium carbonate; (f) solution retarders, such as paraffin; (g) absorption accelerators, such as quaternary ammonium compounds; (h) wetting agents, such as acetyl alcohol and glycerol monostearate; (i) adsorbents, such as kaolin and bentonite; and (j) lubricants, such as talc, calcium stearate, magnesium stearate, solid polyethylene glycols, sodium lauryl sulfate, or mixtures thereof. For capsules, tablets, and pills, the dosage forms may also comprise buffering agents.

Liquid dosage forms for oral administration include pharmaceutically acceptable emulsions, solutions, suspensions, syrups, and elixirs. In addition to the active compounds, the liquid dosage forms may comprise inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, oils, such as cottonseed oil, groundnut oil, corn germ oil, olive oil, castor oil, and sesame oil, glycerol, tetrahydrofurfuryl alcohol, polyethyleneglycols, fatty acid esters of sorbitan, or mixtures of these substances, and the like.

Besides such inert diluents, the composition can also include adjuvants, such as wetting agents, emulsifying and suspending agents, sweetening, flavoring, and perfuming agents.

Actual dosage levels of active ingredients in the compositions of the embodiments may be varied to obtain an amount of NTP peptide and additional active agent that is effective to obtain a desired therapeutic response for a particular composition and method of administration. The selected dosage level therefore depends upon the desired therapeutic effect, the route of administration, the desired duration of treatment, and other factors.

With mammals, including humans, the effective amounts can be administered on the basis of body surface area. The interrelationship of dosages for animals of various sizes, species and humans (based on mg/$M^2$ of body surface) is described by E. J. Freireich et al., Cancer Chemother. Rep., 50 (4):219 (1966). Body surface area may be approximately determined from the height and weight of an individual (see e.g., Scientific Tables, Geigy Pharmaceuticals, Ardsley, N.Y. pp. 537-538 (1970)).

The total daily dose of the NTP peptide and additional active agent administered to a host may be in single or divided doses. Dosage unit compositions may contain such amounts of such submultiples thereof as may be used to make up the daily dose. It will be understood, however, that the specific dose level for any particular patient will depend upon a variety of factors including the body weight, general health, sex, diet, time and route of administration, potency of the administered drug, rates of absorption and excretion, combination with other drugs and the severity of the particular disease being treated. It is preferred that the composition is administered only once as an injection or infusion, or in another preferred embodiment, the composition is administered twice. In this embodiment, the period of time between administration of the composition may vary anywhere from 2 months to 10 years, or from 8 months to 4 years, or more than about one year (e.g., between 1 and 2 years).

A method of administering an NTP peptide composition according to the embodiments includes, but is not limited to, administering the compounds intramuscularly, orally, intravenously, intraperitoneally, intracerebrally (intraparenchymally), intracerebroventricularly, intratumorally, intralesionally, intradermally, intrathecally, intranasally, intraocularly, intraarterially, topically, transdermally, via an aerosol, infusion, bolus injection, implantation device, sustained release system etc.

Another method of administering an NTP peptide of the embodiments is by a transdermal or transcutaneous route. The additional active agent may be employed together with the NTP peptide, or may be administered separately as discussed above, or may not be administered at all. One example of such an embodiment is the use of a patch. In particular, a patch can be prepared with a fine suspension of Peptide in, for example, dimethylsulfoxide (DMSO), or a mixture of DMSO with cottonseed oil and brought into contact with the skin of the tumor carrying mammals away from the tumor location site inside a skin pouch. Other mediums or mixtures thereof with other solvents and solid supports would work equally as well. The patch can contain the Peptide compound in the form of a solution or a suspension. The patch can then be applied to the skin of the patient, for example, by means of inserting it into a skin pouch of the patient formed by folding and holding the skin together by means of stitches, clips or other holding devices. This pouch should be employed in such a manner so that continuous contact with the skin is assured without the interference of the mammal. Besides using a skin pouch, any device can be used which ensures the firm placement of the patch in contact with the skin. For instance, an adhesive bandage could be used to hold the patch in place on the skin.

NTP peptides, optionally in combination with an additional active agent, may be administered in a sustained release formulation or preparation. Suitable examples of sustained-release preparations include semipermeable polymer matrices in the form of shaped articles, e.g. films, or microcapsules. Sustained release matrices include polyesters, hydrogels, polylactides (U.S. Pat. No. 3,773,919, EP 58,481), copolymers of L-glutamic acid and gamma ethyl-L-glutamate (Sidman et al., Biopolymers, 22: 547-556), poly(2-hydroxyethyl-methacrylate) (Langer et al., J. Biomed. Mater. Res., 15: 167-277 and Langer, Chem. Tech., 12: 98-105), ethylene vinyl acetate (Langer et al., supra) or poly-D(−)-3-hydroxybutyric acid (EP 133,988). Sustained-release compositions also may include liposomes, which can be prepared by any of several methods known in the art (e.g., Eppstein et al., Proc. Natl. Acad. Sci. USA, 82: 3688-3692; EP 36,676; EP 88,046; and EP 143,949).

Another method of administering an NTP peptide of the embodiments is by direct or indirect infusion of the NTP peptide into the tumor or other tissue to be treated. One example of such an embodiment is the direct injection of NTP peptide into the tumor or other tissue to be treated. The treatment may consist of a single injection, multiple injections on one occasion or a series of injections over a period of hours, days or months with the regression or destruction of the tumor or other tissue to be treated being monitored by means of biopsy, imaging or other methods of monitoring tissue growth. The injection into the tumor or other tissue to be treated may be by a device inserted into an orifice such as the nose, mouth, ear, vagina, rectum or urethra or through an incision in order to reach the tumor or tissue in vivo and may performed in conjunction with an imaging or optical system such as ultrasound or fibre optic scope in order to identify the appropriate site for the injection(s). Another example of such an embodiment is the use of a device that can provide a constant infusion of NTP peptide to the tissue over time.

Another method of administering an NTP peptide is in conjunction with a surgical or similar procedure employed to physically excise, ablate or otherwise kill or destroy tumor or other tissue or cellular elements required or desired to be removed or destroyed wherein an NTP peptide of the embodiments is administered to the immediate area(s) surrounding the area(s) where the tumor or other tissue was removed in order to destroy or impede the growth of any tumor cells or other cellular elements not removed or destroyed by the procedure Another method of administering an NTP peptide of the embodiments is by implantation of a device within the tumor or other tissue to be treated. In this embodiment, the additional active agent typically will be administered via a different route of administration than the NTP peptide. One example of such an embodiment is the implantation of a wafer containing Peptide in the tumor or other tissue to be treated, and the administration of the additional active agent via oral administration. The wafer releases a therapeutic dose of NTP peptide into the tissue over time. Alternatively or additionally, the composition may be administered locally via implantation into the affected area of a membrane, sponge, or other appropriate material on to which the NTP peptide has been absorbed. Where an implantation device is used, the device may be implanted into any suitable tissue or organ, and delivery of the Peptide may be directly through the device via bolus, or via continuous administration, or via catheter using continuous infusion.

An alternative method of administration is to introduce one or more copies of an NTP peptide-encoding gene into the cell being targeted and, if necessary, inducing the copy(ies) of the gene to begin producing Peptide intracellularly. In this embodiment, the additional active agent typically will be administered via a different route of administration than the NTP peptide. One manner in which gene therapy can be applied is to use the NTP peptide-encoding gene (either genomic DNA, cDNA, and/or synthetic DNA encoding the Peptide (or a fragment, variant, homologue or derivative thereof)) which may be operably linked to a constitutive or inducible promoter to form a gene therapy DNA construct. The promoter may be homologous or heterologous to an endogenous Peptide-encoding gene, provided that it is active in the cell or tissue type into which the construct will be inserted. Other components of the gene therapy DNA construct may optionally include, as required, DNA molecules designed for site-specific integration (e.g., endogenous flanking sequences useful for homologous recombination), tissue-specific promoter, enhancer(s) or silencer(s), DNA molecules capable of providing a selective advantage over the parent cell, DNA molecules useful as labels to identify transformed cells, negative selection systems, cell specific binding agents (as, for example, for cell targeting) cell-specific internalization factors, and transcription factors to enhance expression by a vector as well as factors to enable vector manufacture.

Means of gene delivery to a cell or tissue in vivo or ex vivo include (but are not limited to) direct injection of bare DNA, ballistic methods, liposome-mediated transfer, receptor-mediated transfer (ligand-DNA complex), electroporation, and calcium phosphate precipitation. See U.S. Pat. No. 4,970,154, WO 96/40958, U.S. Pat. No. 5,679,559, U.S. Pat. No. 5,676,954, and U.S. Pat. No. 5,593,875, the disclosures of each of which are incorporated by reference herein in their entirety. They also include use of a viral vector such as a retrovirus, adenovirus, adeno-associated virus, pox virus, lentivirus, papilloma virus or herpes simplex virus, use of a DNA-protein conjugate and use of a liposome. The use of gene therapy vectors is described, for example, in U.S. Pat. No. 5,672,344, U.S. Pat. No. 5,399,346, U.S. Pat. No. 5,631,236, and U.S. Pat. No. 5,635,399, the disclosures of each of which are incorporated by reference herein in their entirety.

The NTP peptide-encoding gene may be delivered through implanting into patients certain cells that have been genetically engineered ex vivo, using methods such as those described herein, to express and secrete the NTP peptide or fragments, variants, homologues, or derivatives thereof. Such cells may be animal or human cells, and may be derived from the patient's own tissue or from another source, either human or non-human. Optionally, the cells may be immortalized or be stem cells. However, in order to decrease the chance of an immunological response, it is preferred that the cells be encapsulated to avoid infiltration of surrounding tissues. The encapsulation materials are typically biocompatible, semi-permeable polymeric enclosures or membranes that allow release of the protein product(s) but prevent destruction of the cells by the patient's immune system or by other detrimental factors from the surrounding tissues. Methods used for membrane encapsulation of cells are familiar to the skilled artisan, and preparation of encapsulated cells and their implantation in patients may be accomplished without undue experimentation. See, e.g., U.S. Pat. Nos. 4,892,538; 5,011,472; and 5,106,627, the disclosures of each of which are incorporated by reference herein in their entirety. A system for encapsulating living cells is described in PCT WO 91/10425. Techniques for formulating a variety of other sustained or controlled delivery means, such as liposome carriers, bio-erodible particles or beads, are also known to those in the art, and are described, for example, in U.S. Pat. No. 5,653,975, the disclosure of which is incorporated by reference herein in their entirety. The cells, with or without encapsulation, may be implanted into suitable body tissues or organs of the patient.

In certain embodiments, the invention provides a method of reducing the incidence of clinically detected prostate cancer in mammals, including mammals suffering from BPH, which comprises administering to the mammal at least once, a therapeutically effective amount of an NTP peptide, specifically an isolated peptide comprising the amino acid sequence in SEQ ID NO. 66 (Ile-Asp-Gln-Gln-Val-Leu-Ser-Arg-Ile-Lys-Leu-Glu-Ile-Lys-Arg-Cys-Leu). In other embodiments, the invention provides a method of preventing or reducing the progression of prostate cancer in mammals at risk of developing clinically detected prostate cancer, which comprises administering to the mammal a therapeutically effective amount of an NTP peptide, specifically an isolated peptide comprising the amino acid sequence in SEQ ID NO. 66 (Ile-Asp-Gln-Gln-Val-Leu-Ser-Arg-Ile-Lys-Leu-Glu-Ile-Lys-Arg-Cys-Leu).

In certain embodiments, the isolated peptide comprising the amino acid sequence in SEQ ID NO. 66 is administered in combination with at least one active agent selected from the group consisting of (1) of an inhibitor of 5α-reductase and/or an antiestrogen, (2) an inhibitor of 5α-reductase and/or an aromatase inhibitor, (3) a 5α-reductase inhibitor and/or a 17β-HSD inhibitor, (4) a 5α-reductase inhibitor, an antiestrogen and an aromatase inhibitor, (5) a 5α-reductase inhibitor, an antiestrogen and a 17β-HSD inhibitor, (6) a 5α-reductase inhibitor, an aromatase inhibitor, an antiestrogen and a 17β-HSD inhibitor, (7) a 5α-reductase inhibitor, an antiandrogen and an antiestrogen, (8), a 5α-reductase inhibitor, an antiandrogen and an aromatase inhibitor, (9) a 5α-reductase inhibitor, an antiandrogen and an 17β-HSD inhibitor, (10) a 5α-reductase inhibitor, an antiandrogen, an antiestrogen and an aromatase inhibitor, (11) a 5α-reductase inhibitor, an antiandrogen, an aromatase inhibitor and a 17β-HSD inhibitor, (12) a 5α-reductase inhibitor, an antiandrogen, an aromatase inhibitor, an antiestrogen and a 17β-HSD inhibitor, (13) a 17β-HSD inhibitor and an antiestrogen, (14) a 17β-HSD inhibitor and an aromatase inhibitor, (15) a 17β-HSD inhibitor, an aromatase inhibitor and an antiestrogen, (16) a 17β-HSD inhibitor, an antiandrogen and an antiestrogen, (17) a 17β-HSD inhibitor, an antiandrogen and an aromatase inhibitor, (18) a 17β-HSD inhibitor, an antiandrogen, an antiestrogen and an aromatase inhibitor, (19) an antiestrogen and an aromatase inhibitor and (20) an antiestrogen, an aromatase inhibitor, and an antiandrogen, (21) an LHRH agonist or antagonist, an inhibitor of 5α-reductase and an antiestrogen, (22) an LHRH agonist or antagonist, an inhibitor of 5α-reductase and an aromatase inhibitor, (23) an LHRH agonist or antagonist, a 5α reductase inhibitor and a 17β-HSD inhibitor, (24) an LHRH agonist or antagonist, a 5α-reductase inhibitor, an antiestrogen and an aromatase inhibitor, (25) an LHRH agonist or antagonist, a 5α-reductase inhibitor, an antiestrogen and a 17β-HSD inhibitor, (26) an LHRH agonist or antagonist, a 5α-reductase inhibitor, an aromatase inhibitor, an antiestrogen and a 17β-HSD inhibitor, (27) an LHRH agonist or antagonist, a 5α-reductase inhibitor, an antiandrogen and an antiestrogen, (28), an LHRH agonist or antagonist, a 5α-reductase inhibitor, an antiandrogen and an aromatase inhibitor, (29) an LHRH agonist or antagonist, a 5α-reductase inhibitor, an antiandrogen and an 17β-HSD inhibitor, (30) an LHRH agonist or antagonist, a 5α-reductase inhibitor, an antiandrogen, an antiestrogen and an aromatase inhibitor, (31) an LHRH agonist or antagonist, a 5α-reductase inhibitor, an antiandrogen, an aromatase inhibitor and a 17β-HSD inhibitor, (32) an LHRH agonist or antagonist, a 5α-reductase inhibitor, an antiandrogen, an aromatase inhibitor, an antiestrogen and a 17β-HSD inhibitor, (33) an LHRH agonist or antagonist, a 17β-HSD inhibitor and an antiestrogen, (34) an LHRH agonist or antagonist, a 17β-HSD inhibitor and an aromatase inhibitor, (35) an LHRH agonist or antagonist, a 17β-HSD inhibitor, an aromatase inhibitor and an antiestrogen, (36) an LHRH agonist or antagonist, a 17β-HSD inhibitor, an antiandrogen and an antiestrogen, (37) an LHRH agonist or antagonist, a 17β-HSD inhibitor, an antiandrogen and an aromatase inhibitor, (38) an LHRH agonist or antagonist, a 17β-HSD inhibitor, an antiandrogen, an antiestrogen and an aromatase inhibitor, (39) an LHRH agonist or antagonist, an antiestrogen and an aromatase inhibitor and (40) an LHRH agonist or antagonist, an antiestrogen, an aromatase inhibitor, and an antiandrogen.

The following examples are provided to illustrate the present embodiments. It should be understood, however, that the embodiments are not to be limited to the specific conditions or details described in these examples. Throughout the specification, any and all references to a publicly available document, including a U.S. patent, are specifically incorporated by reference. In particular, the embodiments expressly incorporate by reference the examples contained in pending U.S. patent application Ser. No. 14/808,713, filed Jul. 24, 2015, entitled: METHODS OF REDUCING THE NEED FOR SURGERY IN PATIENTS SUFFERING FROM BENIGN PROSTATIC HYPERPLASIA; U.S. patent application Ser. No. 14/606,683, filed Jan. 27, 2015, entitled: METHOD OF TREATING DISORDERS REQUIRING DESTRUCTION OR REMOVAL OF CELLS, U.S. application Ser. No. 14/738,551, filed Jun. 12, 2015, entitled: COMBINATION COMPOSITIONS FOR TREATING DISORDERS REQUIRING REMOVAL OR DESTRUCTION OF UNWANTED CELLULAR PROLIFERATIONS, U.S. patent application Publication Nos. 2007/0237780 (now abandoned); 2003/0054990 (now U.S. Pat. No. 7,172,893); 2003/0096350 (now U.S. Pat. No. 6,924,266); 2003/0096756 (now U.S. Pat. No. 7,192,929); 2003/0109437 (now U.S. Pat. No. 7,241,738); 2003/0166569 (now U.S. Pat. No. 7,317,077); 2005/0032704 (now U.S. Pat. No. 7,408,021); and 2015/0148303 (now U.S. Pat. No. 9,243,035), each of which reveal that certain peptides specified therein are effective agents for causing cell death in vivo in normal rodent muscle tissue, subcutaneous connective tissue, dermis and other tissue.

Example One

In a series of clinical studies undertaken between 2009 and 2016 a total of 628 men with benign prostatic hyperplasia (BPH) received SEQ ID NO. 66 (Ile-Asp-Gln-Gln-Val-Leu-Ser-Arg-Ile-Lys-Leu-Glu-Ile-Lys-Arg-Cys-Leu), 2.5 mg given by intraprostatic injection into the transition zone of the prostate to treat the symptoms of BPH and were subsequently followed clinically and by laboratory testing. After intervals up to 6.5 years after injection, all available patients were followed urologically at specialized clinics with investigation of BPH symptoms and events of disease progression and safety assessments. All cases of clinically or biopsy detected prostate cancer were documented. The incidence of new biopsy or surgically proven prostate cancer after 12 months and overall was compared to the incidence of detected prostate cancer in large long-term clinical trials in the medical literature. Although a) the treatments were for BPH; b) the injections were directed at the central part of the prostate where cancer is less common; and c) the injections consisted of only a single or two injection(s) of SEQ ID NO. 66, the incidence of prostate cancer compared to the known expected incidence of 2-25% was surprisingly reduced in these patients to 0-1.3%. The results can be found in Table 1 below.

TABLE 1

| Treatment | Number of patients | Incidence of cancer |
| --- | --- | --- |
| SEQ ID NO: 66[1] | 628 | 0.8% |
| Control[2] | | >20% |

[1]Excludes patients diagnosed with prostate cancer in first 12 months of study. Incidence of clinically detected cancer from inclusion of patients diagnosed with prostate cancer in first 12 months of study was 1.3%;
[2]Long term trial outcome results in BPH populations from published studies. (Thompson, IM, et al., "The Influence of Finasteride on the Development of Prostate Cancer," *N Engl J Med*, Vol. 349, pp. 215-224 (2003); Andriole GL, et al., "Effect of Dutasteride on the Risk of Prostate Cancer," *N Engl J Med*, Vol. 362, pp. 1192-1202 (2010)).

Based on the results of these studies, administering the NTP peptides of the present invention to patients requiring treatment for, or susceptible to developing, prostate cancer, and/or administration to portions of the prostate where cancer is more common, would be expected to have an even more pronounced effect in preventing the incidence of prostate cancer, as well as preventing or reducing the progression of prostate cancer in patients susceptible to developing prostate cancer as determined by one or more prostate cancer screening techniques. The claimed compositions therefore are useful in treating a patient population different from only those suffering from BPH, and are useful in preventing the incidence of prostate cancer, as well as preventing or reducing the progression of prostate cancer in patients susceptible to developing prostate cancer as determined by one or more prostate cancer screening techniques for this patient population.

Example Two

In a series of clinical studies undertaken between 2009 and 2016, a total of 816 men with benign prostatic hyperplasia (BPH) received SEQ ID NO. 66 (Ile-Asp-Gln-Gln-Val-Leu-Ser-Arg-Ile-Lys-Leu-Glu-Ile-Lys-Arg-Cys-Leu), 2.5 mg (n=628) or vehicle alone injections of sterile saline solution (n=188) given by intraprostatic injection into the transition zone of the prostate to treat the symptoms of BPH, were subsequently followed clinically and by laboratory testing. After intervals up to 6.5 years after injection, all available patients were followed urologically at specialized clinics with investigation of BPH symptoms and events of disease progression and safety assessments. All cases of clinically or biopsy detected prostate cancer were documented. The incidence of new biopsy or surgically proven prostate cancer after 12 months and overall was compared to the incidence of detected prostate cancer in the patients receiving the sterile saline solution (control). Although a) the treatments were for BPH; b) the injections were directed at the central part of the prostate where cancer is less common; and c) the injections consisted of only a single or two injection(s) of SEQ ID NO. 66, the incidence of prostate cancer in the subjects treated in accordance with the present invention was unexpectedly much lower than that of the control population. The results are shown in Table 2 below.

TABLE 2

| Treatment | Number of patients | Incidence of cancer[1] |
|---|---|---|
| SEQ ID NO: 66[2] | 628 | 0.8%* |
| Control[1] | 188 | 2.7% |

[1]Excludes patients diagnosed with prostate cancer in first 12 months of study.
[2]Incidence of clinically detected cancer from inclusion of patients diagnosed with prostate cancer in first 12 months of study was 1.3%;
*p < .05

Based on the results of these studies, administering the NTP peptides of the present invention to patients requiring treatment for, or susceptible to developing, prostate cancer, and/or administration to portions of the prostate where cancer is more common, would be expected to have an even more pronounced effect in preventing the incidence of prostate cancer, as well as preventing or reducing the progression of prostate cancer in patients susceptible to developing prostate cancer as determined by one or more prostate cancer screening techniques. The claimed compositions therefore are useful in treating a patient population different from only those suffering from BPH, and are useful in preventing the incidence of prostate cancer, as well as preventing or reducing the progression of prostate cancer in patients susceptible to developing prostate cancer as determined by one or more prostate cancer screening techniques for this patient population.

Example Three

In a series of clinical studies undertaken between 2009 and 2016 a total of 628 men with benign prostatic hyperplasia (BPH) received SEQ ID NO. 66 (Ile-Asp-Gln-Gln-Val-Leu-Ser-Arg-Ile-Lys-Leu-Glu-Ile-Lys-Arg-Cys-Leu), 2.5 mg given by intraprostatic injection into the transition zone of the prostate to treat the symptoms of BPH and were subsequently followed clinically and by laboratory testing. After intervals up to 6.5 years after injection, all available patients were followed urologically at specialized clinics with investigation of BPH symptoms and events of disease progression and safety assessments. All cases of clinically or biopsy detected prostate cancer were documented. The incidence of new biopsy or surgically proven prostate cancer of Gleason Grade>=7 was compared to the incidence of detected prostate cancer in large long-term clinical trials in the medical literature. Although a) the treatments were for BPH; b) the injections were directed at the central part of the prostate where cancer is less common; and c) the injections consisted of only a single or two injection(s) of SEQ ID NO. 66, the incidence of prostate cancer compared to the known expected incidence of 5-6% was surprisingly reduced in these patients to <0.3%. The results can be found in Table 3 below.

TABLE 3

| Treatment | Number of patients | Incidence of cancer (Gleason Grade >= 7) |
|---|---|---|
| SEQ ID NO: 66 | 628 | <0.3% |
| Control[1] | | 5-6% |

[1]Long term trial outcome results in BPH populations from published studies. (Thompson, IM, et al., "The Influence of Finasteride on the Development of Prostate Cancer," N Engl J Med, Vol.349, pp. 215-224 (2003); Andriole GL, et al., "Effect of Dutasteride on the Risk of Prostate Cancer," N Engl J Med, Vol. 362, pp. 1192-1202 (2010)).

Based on the results of these studies, administering the NTP peptides of the present invention to patients requiring treatment for, or susceptible to developing, prostate cancer, and/or administration to portions of the prostate where cancer is more common, would be expected to have an even more pronounced effect in preventing the incidence of prostate cancer, as well as preventing or reducing the progression of prostate cancer in patients susceptible to developing prostate cancer as determined by one or more prostate cancer screening techniques. The claimed compositions therefore are useful in treating a patient population different from only those suffering from BPH, and are useful in preventing the incidence of prostate cancer, as well as preventing or reducing the progression of prostate cancer in patients susceptible to developing prostate cancer as determined by one or more prostate cancer screening techniques for this patient population.

The results from the foregoing examples illustrate the unexpectedly superior effect of the NTP peptides, in reducing the incidence of clinically detected prostate cancer, and in preventing or reducing the progression of prostate cancer in patients susceptible to developing prostate cancer as determined by one or more prostate cancer screening techniques. It will be apparent to those skilled in the art that various modifications and variations can be made in the methods and compositions of the present embodiments without departing from the spirit or scope of the embodiments.

What is claimed is:

1. A method of reducing the onset of prostate cancer in a mammal susceptible to developing prostate cancer as determined by one or more prostate cancer screening techniques, comprising administering, more than once, to the mammal susceptible to developing prostate cancer a therapeutically effective amount of an isolated peptide comprising the amino acid sequence in SEQ ID NO. 66 (Ile-Asp-Gln-Gln-Val-Leu-Ser-Arg-Ile-Lys-Leu-Glu-Ile-Lys-Arg-Cys-Leu), wherein the method reduces the onset of prostate cancer by an amount greater than about 15%, when compared to mammals receiving a placebo.

2. The method of claim 1, wherein the method comprises administration of a therapeutically effective amount of at least one of the peptides as claimed in claim 1 and a carrier.

3. The method of claim 1, wherein the method comprises administration of a therapeutically effective amount of at least one of the peptides as claimed in claim 1 and at least one and up to 25 additional amino acids flanking either the N-terminus or C-terminus of the isolated peptide of claim 1.

4. The method of claim 1, wherein the peptide is administered by a method selected from the group consisting of orally, subcutaneously, intradermally, intranasally, intravenously, intramuscularly, intrathecally, intranasally, intratumorally, topically, and transdermally.

5. The method of claim 1, wherein the method provides an onset of prostate cancer in a range of from about 0% to about 5%.

6. The method of claim 5, wherein the method provides an onset of prostate cancer in a range of from about 0% to about 2%.

7. The method of claim 5, wherein the method provides an onset of prostate cancer in a range of from about 0% to about 1.3%.

8. A method of reducing the progression of prostate cancer in a mammal susceptible to developing prostate cancer as determined by one or more prostate cancer screening techniques, comprising administering, more than once, to the mammal a therapeutically effective amount of an isolated peptide comprising the amino acid sequence in SEQ ID NO. 66 (Ile-Asp-Gln-Gln-Val-Leu-Ser-Arg-Ile-Lys-Leu-Glu-Ile-Lys-Arg-Cys-Leu), wherein the method reduces the progression of prostate cancer to an amount within the range of from about 0% to less than about 5%.

9. The method of claim 8, wherein the method comprises administration of a therapeutically effective amount of at least one of the peptides as claimed in claim 8, and a carrier.

10. The method of claim 8, wherein the method comprises administration of a therapeutically effective amount of at least one of the peptides as claimed in claim 8 and at least one and up to 25 additional amino acids flanking either the N-terminus or C-terminus of the isolated peptide of claim 8.

11. The method of claim 8, wherein the peptide is administered by a method selected from the group consisting of orally, subcutaneously, intradermally, intranasally, intravenously, intraprostatically, intramuscularly, intrathecally, intranasally, intratumorally, topically, and transdermally.

12. The method of claim 8, wherein the method reduces the progression of prostate cancer to an amount within the range about 0% to about 1%.

13. The method of claim 8, wherein the method reduces the progression of prostate cancer to an amount of about 0%.

14. The method of claim 8, wherein the mammal susceptible to developing prostate cancer had a baseline PSA level of ≥2.5.

* * * * *

SEQUENCE LISTING

<160> NUMBER OF SEQ ID NOS: 118

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Met Glu Phe Ser Leu Leu Leu Pro Arg Leu Glu Cys Asn Gly Ala
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Ala Ile Ser Ala His Arg Asn Leu Arg Leu Pro Gly Ser Ser
1               5                   10                  15

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asp Ser Pro Ala Ser Ala Ser Pro Val Ala Gly Ile Thr Gly Met Cys
1               5                   10                  15

Thr

<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Met Cys Thr His Ala Arg Leu Ile Leu Tyr Phe Phe Leu Val Glu Met
1               5                   10                  15

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Phe Phe Leu Val Glu Met Glu Phe Leu His
1               5                   10

<210> SEQ ID NO 6
<211> LENGTH: 11
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 6

Val Gly Gln Ala Gly Leu Glu Leu Pro Thr Ser
1               5                   10

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asp Asp Pro Ser Val Ser Ala Ser Gln Ser Ala Arg Tyr Arg Thr Gly
1               5                   10                  15

His

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Thr Gly His His Ala Arg Leu Cys Leu Ala Asn Phe Cys Gly
1               5                   10

<210> SEQ ID NO 9
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala Asn Phe Cys Gly Arg Asn Arg Val Ser Leu Met Cys Pro Ser Trp
1               5                   10                  15

Ser

<210> SEQ ID NO 10
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Pro Glu Leu Lys Gln Ser Thr Cys Leu Ser Leu Pro Lys Cys Trp Asp
1               5                   10                  15

Tyr Arg Arg

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 11

Leu Lys Gln Ser Thr Cys Leu Ser Leu Pro Lys Cys Trp Asp Tyr Arg
1               5                   10                  15

Arg

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ser Thr Cys Leu Ser Leu Pro Lys Cys Trp Asp Tyr Arg Arg
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Leu Ser Leu Pro Lys Cys Trp Asp Tyr Arg Arg
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Lys Cys Trp Asp Tyr Arg Arg Ala Ala Val Pro Gly Leu
1               5                   10

<210> SEQ ID NO 15
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Lys Cys Trp Asp Tyr Arg Arg Ala Ala Val Pro Gly Leu Phe Ile Leu
1               5                   10                  15

Phe Phe Leu

<210> SEQ ID NO 16
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Lys Cys Trp Asp Tyr Arg Arg Ala Ala Val Pro Gly Leu Phe Ile Leu
1               5                   10                  15

Phe Phe Leu Arg His Arg Cys Pro
            20

<210> SEQ ID NO 17
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Lys Cys Trp Asp Tyr Arg Arg Ala Ala Val Pro Gly Leu Phe Ile Leu
1               5                   10                  15

Phe Phe Leu Arg His Arg Cys Pro Thr Leu Thr Gln Asp Glu Val Gln
            20                  25                  30

Trp Cys Asp His Ser Ser
            35

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Trp Asp Tyr Arg Arg
1               5

<210> SEQ ID NO 19
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Phe Ile Leu Phe Phe Leu Arg His Arg Cys Pro Thr Leu
1               5                   10

<210> SEQ ID NO 20
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Phe Ile Leu Phe Phe Leu Arg His Arg Cys Pro Thr Leu Thr Gln Asp
1               5                   10                  15

Glu Val Gln Trp Cys Asp His Ser Ser
            20                  25

<210> SEQ ID NO 21
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

-continued

His Arg Cys Pro Thr Leu Thr Gln Asp Glu Val Gln Trp Cys Asp His
1               5                   10                  15

Ser Ser Leu Gln Pro Ser Thr Pro Glu Ile Lys His Pro
            20                  25

<210> SEQ ID NO 22
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Pro Ala Ser Ala Ser Gln Val Ala Gly Thr Lys Asp Met His
1               5                   10

<210> SEQ ID NO 23
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Asp Met His His Tyr Thr Trp Leu Ile Phe Ile Phe Ile Phe Asn Phe
1               5                   10                  15

Leu Arg

<210> SEQ ID NO 24
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

His Tyr Thr Trp Leu Ile Phe Ile Phe Ile Phe Asn Phe Leu Arg Gln
1               5                   10                  15

Ser Leu Asn

<210> SEQ ID NO 25
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Ser Val Thr Gln Ala Gly Val Gln Trp Arg Asn Leu Gly Ser Leu Gln
1               5                   10                  15

Pro Leu Pro Pro Gly Phe Lys Leu Phe Ser Cys Pro Ser Leu Leu Ser
            20                  25                  30

Ser Trp Asp Tyr Arg Arg Pro Pro Arg Leu Ala Asn Phe
        35                  40                  45

<210> SEQ ID NO 26
<211> LENGTH: 19
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 26

Pro Gly Phe Lys Leu Phe Ser Cys Pro Ser Leu Leu Ser Ser Trp Asp
1               5                   10                  15

Tyr Arg Arg

<210> SEQ ID NO 27
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Phe Lys Leu Phe Ser Cys Pro Ser Leu Leu Ser Ser Trp Asp Tyr Arg
1               5                   10                  15

Arg Pro Pro Arg Leu Ala Asn Phe
            20

<210> SEQ ID NO 28
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Phe Ser Cys Pro Ser Leu Leu Ser Ser Trp Asp Tyr Arg Arg
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ser Leu Leu Ser Ser Trp Asp Tyr Arg Arg
1               5                   10

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ser Ser Trp Asp Tyr
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31
```

Ser Ser Trp Asp Tyr Arg Arg
1               5

<210> SEQ ID NO 32
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ser Ser Trp Asp Tyr Arg Arg Pro Pro Arg Leu Ala Asn Phe Phe Val
1               5                   10                  15

Phe Leu Val Glu Met Gly Phe Thr Met
            20                  25

<210> SEQ ID NO 33
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Phe Val Phe Leu Val Glu Met Gly Phe Thr Met
1               5                   10

<210> SEQ ID NO 34
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Met Gly Phe Thr Met Phe Ala Arg Leu Ile Leu Ile Ser Gly Pro Cys
1               5                   10                  15

Asp Leu Pro Ala Ser Ala Ser
            20

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ile Ser Gly Pro Cys
1               5

<210> SEQ ID NO 36
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Asp Leu Pro Ala Ser Ala Ser Gln Ser Ala Gly Ile Thr Gly Val Ser
1               5                   10                  15

His

<210> SEQ ID NO 37
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Val Ser His His Ala Arg Leu Ile Phe Asn Phe Cys Leu Phe Glu
1               5                   10                  15

Met

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Asn Phe Cys Leu Phe Glu Met Glu Ser His
1               5                   10

<210> SEQ ID NO 39
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Ser Val Thr Gln Ala Gly Val Gln Trp Pro Asn Leu Gly Ser Leu Gln
1               5                   10                  15

Pro Leu Pro Pro Gly Leu Lys Arg Phe Ser Cys Leu Ser Leu Pro Ser
                20                  25                  30

Ser Trp Asp Tyr Gly His Leu Pro Pro His Pro Ala Asn Phe
            35                  40                  45

<210> SEQ ID NO 40
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Pro Pro Gly Leu Lys Arg Phe Ser Cys Leu Ser Leu Pro Ser Ser Trp
1               5                   10                  15

Asp Tyr Gly

<210> SEQ ID NO 41
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Phe Ser Cys Leu Ser Leu Pro Ser Ser Trp Asp Tyr Gly His
1               5                   10

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Leu Ser Leu Pro Ser Ser Trp Asp Tyr
1               5

<210> SEQ ID NO 43
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Ser Ser Trp Asp Tyr Gly His Leu Pro Pro His Pro Ala Asn Phe Cys
1               5                   10                  15

Ile Phe Ile Arg Gly Gly Val Ser Pro Tyr Leu Ser Gly Trp Ser Gln
            20                  25                  30

Thr Pro Asp Leu Arg
        35

<210> SEQ ID NO 44
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Pro Gly Phe Phe Lys Leu Phe Ser Cys Pro Ser Leu Leu Ser Ser Trp
1               5                   10                  15

Asp Tyr Arg Arg
            20

<210> SEQ ID NO 45
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Pro Glu Leu Lys Gln Ser Thr Cys Leu Ser Leu Pro Lys Cys Trp Asp
1               5                   10                  15

Tyr Arg Arg

<210> SEQ ID NO 46
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 46

Pro Pro Gly Leu Lys Arg Phe Ser Cys Leu Ser Leu Pro Ser Ser Trp
1               5                   10                  15

Asp Tyr Gly

<210> SEQ ID NO 47
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Phe Ser Cys Leu Ser Leu Pro Ser Ser Trp Asp Tyr Gly His
1               5                   10

<210> SEQ ID NO 48
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ser Thr Cys Leu Ser Leu Pro Lys Cys Trp Asp Tyr Arg Arg
1               5                   10

<210> SEQ ID NO 49
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Phe Ser Cys Pro Ser Leu Leu Ser Ser Trp Asp Tyr Arg Arg
1               5                   10

<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Leu Ser Leu Pro Ser Ser Trp Asp Tyr
1               5

<210> SEQ ID NO 51
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Leu Ser Leu Pro Lys Cys Trp Asp Tyr Arg Arg
1               5                   10
```

```
<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ser Leu Leu Ser Ser Trp Asp Tyr Arg Arg
1               5                   10

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Leu Pro Ser Ser Trp Asp Tyr Arg Arg
1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ser Ser Trp Asp Tyr Arg Arg
1               5

<210> SEQ ID NO 55
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ser Ser Trp Asp Tyr
1               5

<210> SEQ ID NO 56
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ser Ser Trp Asp Tyr Arg Arg Phe Ile Leu Phe Phe Leu
1               5                   10

<210> SEQ ID NO 57
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57
```

```
Trp Asp Tyr Arg Arg Phe Ile Phe Asn Phe Leu
1               5                   10
```

<210> SEQ ID NO 58
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

```
Phe Asn Phe Cys Leu Phe
1               5
```

<210> SEQ ID NO 59
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

```
Phe Ile Phe Asn Phe Leu
1               5
```

<210> SEQ ID NO 60
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

```
Pro Ala Ser Ala Ser Pro Val Ala Gly Ile Thr Gly Met
1               5                   10
```

<210> SEQ ID NO 61
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

```
Pro Ala Ser Ala Ser Gln Val Ala Gly Thr Lys Asp Met
1               5                   10
```

<210> SEQ ID NO 62
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

```
Pro Ala Ser Ala Ser Gln Ser Ala Gly Ile Thr Gly Val
1               5                   10
```

<210> SEQ ID NO 63
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 63

Pro Ala Ser Ala Ser Pro Val Ala Gly
1               5

<210> SEQ ID NO 64
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Phe Phe Leu Val Glu Met
1               5

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ser Val Thr Gln Ala Gly Val Gln Trp
1               5

<210> SEQ ID NO 66
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Ile Asp Gln Gln Val Leu Ser Arg Ile Lys Leu Glu Ile Lys Arg Cys
1               5                   10                  15

Leu

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Leu Ser Arg Ile Lys Leu Glu Ile Lys
1               5

<210> SEQ ID NO 68
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gly Asp His Gly Arg Pro Asn Leu Ser Arg Leu Lys Leu Ala Ile Lys
```

```
1               5                   10                  15
Tyr Glu Val Lys Lys Met
                20

<210> SEQ ID NO 69
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gln Gln Ser Ile Ala Val Lys Phe Leu Ala Val Phe Gly Val Ser Ile
1               5                   10                  15

<210> SEQ ID NO 70
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gly Leu Leu Phe Pro Val Phe Ser Val Cys Tyr Leu Ile Ala Pro Lys
1               5                   10                  15

Ser Pro Leu Gly Leu
                20

<210> SEQ ID NO 71
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Met Met Val Cys Trp Asn Arg Phe Gly Lys Trp Val Tyr Phe Ile
1               5                   10                  15

<210> SEQ ID NO 72
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ser Ala Ile Phe Asn Phe Gly Pro Arg Tyr Leu Tyr His Gly Val
1               5                   10                  15

<210> SEQ ID NO 73
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Pro Phe Tyr Phe Leu Ile Leu Val Arg Ile Ile Ser Phe Leu Ile
1               5                   10                  15
```

```
<210> SEQ ID NO 74
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gly Asp Met Glu Asp Val Leu Leu Asn Cys Thr Leu Leu Lys Arg
1               5                   10                  15

<210> SEQ ID NO 75
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Ser Ser Arg Phe Arg Phe Trp Gly Ala Leu Val Cys Ser Met Asp
1               5                   10                  15

<210> SEQ ID NO 76
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ser Cys Arg Phe Ser Arg Val Ala Val Thr Tyr Arg Phe Ile Thr
1               5                   10                  15

<210> SEQ ID NO 77
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Leu Leu Asn Ile Pro Ser Pro Ala Val Trp Met Ala Arg Asn Thr
1               5                   10                  15

<210> SEQ ID NO 78
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Met Ala Gln Ser Arg Leu Thr Ala Thr Ser Ala Ser Arg Val Gln
1               5                   10                  15

<210> SEQ ID NO 79
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79
```

```
Ala Ile Leu Leu Ser Gln Pro Pro Lys Gln Leu Gly Leu Arg Ala
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Pro Ala Asn Thr Pro Leu Ile Phe Val Phe Ser Leu Glu Ala Gly
1               5                   10                  15

<210> SEQ ID NO 81
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Phe His His Ile Cys Gln Ala Gly Leu Lys Leu Leu Thr Ser Gly
1               5                   10                  15

<210> SEQ ID NO 82
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Asp Pro Pro Ala Ser Ala Phe Gln Ser Ala Gly Ile Thr Gly Val
1               5                   10                  15

<210> SEQ ID NO 83
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Ser His Leu Thr Gln Pro Ala Asn Leu Asp Lys Lys Ile Cys Ser
1               5                   10                  15

<210> SEQ ID NO 84
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Asn Gly Gly Ser Cys Tyr Val Ala Gln Ala Gly Leu Lys Leu Leu Ala
1               5                   10                  15

Ser Cys Asn Pro Ser Lys
            20

<210> SEQ ID NO 85
```

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Met Trp Thr Leu Lys Ser Ser Leu Val Leu Leu Leu Cys Leu Thr
1               5                   10                  15

<210> SEQ ID NO 86
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Cys Ser Tyr Ala Phe Met Phe Ser Ser Leu Arg Gln Lys Thr Ser
1               5                   10                  15

<210> SEQ ID NO 87
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Glu Pro Gln Gly Lys Val Pro Cys Gly Glu His Phe Arg Ile Arg
1               5                   10                  15

<210> SEQ ID NO 88
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gln Asn Leu Pro Glu His Thr Gln Gly Trp Leu Gly Ser Lys Trp
1               5                   10                  15

<210> SEQ ID NO 89
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Leu Trp Leu Leu Phe Ala Val Val Pro Phe Val Ile Leu Lys Cys
1               5                   10                  15

<210> SEQ ID NO 90
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90
```

Gln Arg Asp Ser Glu Lys Asn Lys Val Arg Met Ala Pro Phe Phe
1               5                   10                  15

<210> SEQ ID NO 91
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Leu His His Ile Asp Ser Ile Ser Gly Val Ser Gly Lys Arg Met Phe
1               5                   10                  15

<210> SEQ ID NO 92
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Glu Ala Tyr Tyr Thr Met Leu His Leu Pro Thr Thr Asn Arg Pro
1               5                   10                  15

<210> SEQ ID NO 93
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Lys Ile Ala His Cys Ile Leu Phe Asn Gln Pro His Ser Pro Arg
1               5                   10                  15

<210> SEQ ID NO 94
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Ser Asn Ser His Ser His Pro Asn Pro Leu Lys Leu His Arg Arg
1               5                   10                  15

<210> SEQ ID NO 95
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Ser His Ser His Asn Arg Pro Arg Ala Tyr Ile Leu Ile Thr Ile
1               5                   10                  15

<210> SEQ ID NO 96
<211> LENGTH: 15
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 96

Leu Pro Ser Lys Leu Lys Leu Arg Thr His Ser Gln Ser His His
1               5                   10                  15

<210> SEQ ID NO 97
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Asn Pro Leu Ser Arg Thr Ser Asn Ser Thr Pro Thr Asn Ser Phe Leu
1               5                   10                  15

Met Thr Ser Ser Lys Pro Arg
            20

<210> SEQ ID NO 98
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Ser Ser Ser Leu Gly Leu Pro Lys Cys Trp Asp Tyr Arg His Glu
1               5                   10                  15

<210> SEQ ID NO 99
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Leu Leu Ser Leu Ala Leu Met Ile Asn Phe Arg Val Met Ala Cys
1               5                   10                  15

<210> SEQ ID NO 100
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Thr Phe Lys Gln His Ile Glu Leu Arg Gln Lys Ile Ser Ile Val
1               5                   10                  15

<210> SEQ ID NO 101
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Pro Arg Lys Leu Cys Cys Met Gly Pro Val Cys Pro Val Lys Ile
```

```
<210> SEQ ID NO 102
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Ala Leu Leu Thr Ile Asn Gly His Cys Thr Trp Leu Pro Ala Ser
1               5                   10                  15

<210> SEQ ID NO 103
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Met Phe Val Phe Cys Leu Ile Leu Asn Arg Glu Lys Ile Lys Gly
1               5                   10                  15

<210> SEQ ID NO 104
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gly Asn Ser Ser Phe Phe Leu Leu Ser Phe Phe Phe Ser Phe Gln
1               5                   10                  15

<210> SEQ ID NO 105
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Asn Cys Cys Gln Cys Phe Gln Cys Arg Thr Thr Glu Gly Tyr Ala
1               5                   10                  15

<210> SEQ ID NO 106
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Val Glu Cys Phe Tyr Cys Leu Val Asp Lys Ala Ala Phe Glu Cys Trp
1               5                   10                  15

Trp Phe Tyr Ser Phe Asp Thr
            20

<210> SEQ ID NO 107
<211> LENGTH: 15
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 107

Met Glu Pro His Thr Val Ala Gln Ala Gly Val Pro Gln His Asp
1               5                   10                  15

<210> SEQ ID NO 108
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Leu Gly Ser Leu Gln Ser Leu Leu Pro Arg Phe Lys Arg Phe Ser
1               5                   10                  15

<210> SEQ ID NO 109
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Cys Leu Ile Leu Pro Lys Ile Trp Asp Tyr Arg Asn Met Asn Thr
1               5                   10                  15

<210> SEQ ID NO 110
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Ala Leu Ile Lys Arg Asn Arg Tyr Thr Pro Glu Thr Gly Arg Lys Ser
1               5                   10                  15

<210> SEQ ID NO 111
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Ile Asp Gln Gln Val Leu Ser Arg Ile
1               5

<210> SEQ ID NO 112
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Lys Leu Glu Ile Lys Arg Cys Leu
1               5

```
<210> SEQ ID NO 113
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Val Leu Ser Arg Ile Lys
1               5

<210> SEQ ID NO 114
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Arg Ile Lys Leu Glu Ile Lys
1               5

<210> SEQ ID NO 115
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Val Leu Ser Arg Ile Lys Leu Glu Ile Lys Arg Cys Leu
1               5                   10

<210> SEQ ID NO 116
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Ile Asp Gln Gln Val Leu Ser Arg Ile Lys Leu Glu Ile
1               5                   10

<210> SEQ ID NO 117
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Glu Thr Glu Ser His
1               5

<210> SEQ ID NO 118
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag
```

```
<400> SEQUENCE: 118

His His His His His His
1               5
```